(12) United States Patent
Kubler-Kielb et al.

(10) Patent No.: US 8,795,680 B2
(45) Date of Patent: Aug. 5, 2014

(54) METHODS FOR CONJUGATION OF OLIGOSACCHARIDES OR POLYSACCHARIDES TO PROTEIN CARRIERS THROUGH OXIME LINKAGES VIA 3-DEOXY-D-MANNO-OCTULSONIC ACID

(75) Inventors: Joanna Kubler-Kielb, Bethesda, MD (US); Vince Pozsgay, Washington, DC (US); Teresa Lagergard, Kullavik (SE); Gil Ben-Menachem, Newton, MA (US); Rachel Schneerson, Bethesda, MD (US); Evguenii Vinogradov, Ottawa (CA); Ariel Ginzberg, Rockville, MD (US)

(73) Assignees: The United States of America, as represented by the Secretary, Department of Health and Human Services, Washington, DC (US); National Research Council of Canada, Ottawa (CA)

( * ) Notice: Subject to any disclaimer, the term of this patent is extended or adjusted under 35 U.S.C. 154(b) by 1214 days.

(21) Appl. No.: 12/309,428

(22) PCT Filed: Jul. 18, 2007

(86) PCT No.: PCT/US2007/016373
§ 371 (c)(1),
(2), (4) Date: Jan. 13, 2010

(87) PCT Pub. No.: WO2008/013735
PCT Pub. Date: Jan. 31, 2008

(65) Prior Publication Data
US 2010/0158937 A1 Jun. 24, 2010

Related U.S. Application Data

(60) Provisional application No. 60/832,448, filed on Jul. 21, 2006.

(51) Int. Cl.
*A61K 39/00* (2006.01)

(52) U.S. Cl.
USPC ............... 424/197.11; 424/193.1; 424/194.1; 424/234.1

(58) Field of Classification Search
USPC .................... 424/197.11, 194.1, 193.1, 234.1
See application file for complete search history.

(56) References Cited

U.S. PATENT DOCUMENTS 4,203,970 A * 5/1980 Carlo et al. ................ 424/253.1
4,894,229 A * 1/1990 Polson et al. .............. 424/130.1

(Continued)

FOREIGN PATENT DOCUMENTS

EP 0471954 * 2/1992 ............ A61K 39/10
WO 00/36419 * 6/2000 ........... G01N 33/569

(Continued)

OTHER PUBLICATIONS

Volk, Wesley A et al, The Journal of Biological Chemistry, vol. 247(12), Jun. 25, 1972, pp. 3881-3887.*

(Continued)

*Primary Examiner* — Albert Navarro
*Assistant Examiner* — Ginny Portner
(74) *Attorney, Agent, or Firm* — Klarquist Sparkman LLP

(57) ABSTRACT

Methods for preparing an oligosaccharide-protein carrier immunogenic conjugate or a polysaccharide-protein carrier immunogenic conjugate. The methods include obtaining an oligosaccharide or polysaccharide having a KDO moiety located at the terminal reducing end of the oligosaccharide or polysaccharide that includes a carbonyl functional group; and reacting the carbonyl functional group of the KDO moiety with an aminooxylated protein carrier molecule resulting in a conjugate that includes a covalent oxime bond between the oligosaccharide and the protein carrier or the polysaccharide and the protein carrier.

16 Claims, 8 Drawing Sheets

(56) References Cited

U.S. PATENT DOCUMENTS

| | | | |
|---|---|---|---|
| 5,621,084 A * | 4/1997 | Honda et al. | 536/1.11 |
| 5,880,270 A * | 3/1999 | Berninger et al. | 530/391.9 |
| 5,952,313 A * | 9/1999 | Carlson | 514/53 |
| 5,997,881 A * | 12/1999 | Powell et al. | 424/234.1 |
| 6,020,495 A * | 2/2000 | Sun et al. | 548/202 |
| 6,228,654 B1 * | 5/2001 | Chait et al. | 436/94 |
| 6,465,612 B1 * | 10/2002 | Bertozzi et al. | 530/300 |
| 6,475,754 B1 * | 11/2002 | Bemis et al. | 435/69.1 |
| 6,573,245 B1 * | 6/2003 | Marciani | 514/25 |
| 6,607,725 B2 | 8/2003 | Gu et al. | |
| 6,645,503 B1 * | 11/2003 | Arumugham et al. | 424/197.11 |
| 6,663,869 B1 * | 12/2003 | Rose et al. | 424/193.1 |
| 6,800,728 B2 * | 10/2004 | Schwartz | 530/345 |
| 6,939,945 B2 * | 9/2005 | Bertozzi et al. | 530/300 |
| 7,364,739 B2 * | 4/2008 | Richards et al. | 424/184.1 |
| 7,537,766 B2 * | 5/2009 | Pavliak et al. | 424/184.1 |
| 7,538,092 B2 * | 5/2009 | Orlando et al. | 514/25 |
| 7,723,296 B2 * | 5/2010 | Zhu | 514/17.7 |
| 7,759,070 B2 * | 7/2010 | Cox et al. | 435/7.1 |
| 8,017,739 B2 * | 9/2011 | Eichner et al. | 530/402 |
| 8,030,459 B2 * | 10/2011 | Papisov et al. | 530/409 |
| 8,354,647 B2 * | 1/2013 | Huebner et al. | 250/393 |
| 8,389,565 B2 * | 3/2013 | Pinto et al. | 514/425 |
| 8,440,145 B2 * | 5/2013 | Huebner et al. | 422/500 |
| 2002/0110535 A1 * | 8/2002 | Jones | 424/78.28 |
| 2002/0128381 A1 * | 9/2002 | Jakobsen et al. | 525/54.2 |
| 2002/0146504 A1 * | 10/2002 | Schwartz | 427/2.11 |
| 2002/0169281 A1 * | 11/2002 | Horn et al. | 530/333 |
| 2003/0113769 A1 * | 6/2003 | Manoharan et al. | 435/6 |
| 2004/0224366 A1 * | 11/2004 | Jones et al. | 435/7.1 |
| 2005/0058634 A1 * | 3/2005 | Zhu | 424/94.61 |
| 2005/0147624 A1 * | 7/2005 | Jennings et al. | 424/234.1 |
| 2005/0153057 A1 * | 7/2005 | Richards et al. | 427/2.14 |
| 2005/0169941 A1 | 8/2005 | Lees | |
| 2005/0175620 A1 * | 8/2005 | Jones | 424/178.1 |
| 2005/0266427 A1 * | 12/2005 | Schwartz | 435/6 |
| 2006/0047106 A1 * | 3/2006 | Pavliak et al. | 530/350 |
| 2006/0051812 A1 * | 3/2006 | Helin et al. | 435/7.1 |
| 2008/0008723 A1 * | 1/2008 | Cox et al. | 424/194.1 |
| 2008/0193481 A1 * | 8/2008 | Bundle et al. | 424/204.1 |
| 2009/0028889 A1 * | 1/2009 | Nakaar et al. | 424/186.1 |
| 2009/0047251 A1 * | 2/2009 | Eichner et al. | 424/85.7 |
| 2009/0221449 A1 * | 9/2009 | Defrancq et al. | 506/18 |
| 2010/0047225 A1 * | 2/2010 | Zhu et al. | 424/94.3 |
| 2011/0212125 A1 * | 9/2011 | Robbins et al. | 424/197.11 |
| 2011/0274714 A1 * | 11/2011 | Levine et al. | 424/194.1 |
| 2013/0129776 A1 * | 5/2013 | Levine et al. | 424/197.11 |
| 2013/0302877 A1 * | 11/2013 | Lees, Andrew | 435/188 |

FOREIGN PATENT DOCUMENTS

| | | | | |
|---|---|---|---|---|
| WO | 2004/009082 | * | 1/2004 | A61K 31/4015 |
| WO | 2005/014024 | * | 2/2005 | A61K 38/18 |

OTHER PUBLICATIONS

Singh, Y et al, A novel heterobifunctional linker for facile access to bioconjugates, published on the web Mar. 2, 2006, Organic and Biomolecular Chemistry, pp. 1413-1419.*

Schaeffer, LM et al, Infection and Immunity, vol. 72(12), pp. 7124-7130, Dec. 2004, Interactions of Pulmonary Collectins with *Bordetella bronchiseptica* and *Bordetella pertussis* lipopolysaccharide elucidate the structural bais of their antimicrobial activities.*

Grimmecke, H.D. et al, Glycoconjugate Journal, vol. 15, pp. 555-562, 1998, Studies on the reductive amination of 3-deoxy-D-manno-octulosonic acid (KDO).*

Mieszala, M et al, Carbohdyrate Research, vol. 338, pp. 167-175, 2003, Conjugation of meningococcal lipoligosaccharides through their LipidA terminus conserves their inner epitopes and results in conjugate vaccines having improved immunological properties.*

Middendorf, B et al, Molecular Gen. Genet., Aug. 1999, vol. 262(1), pp. 189-198.*

Melaugh, W. et al, The Journal of Biological Chemistry, vol. 267(19), Jul. 5, 1992, pp. 13434-13439.*

Di Fabio, JL et al, FEMS Microbiology Letters, vol. 97, pp. 275-282, 1992, Characterization of the common antigenic lipopolysaccharide O-chains produced by *Bordetella bronchiseptica* and *Bordetella parapertussis*.*

Joanna Kubler-Kielb, Conjugation of LPS-Derived Oligosaccharides to proteins using oxime chemistry, Chapter 20, Bioconjugation Protocols: Strategies and Methods, Methods in Molecular Biology, vol. 751, 2011, pp. 317-327.*

Auzanneau et al., "Phosphorylated Sugars. Part 27. Synthesis and Reactions, in Acid Medium, of 5-O-Substituted Methyl 3-Deoxy-α-D-manno-oct-w-ulopyranosidonic Acid 4-Phophates," *J. Chem. Soc. Perkin Trans* 1 509-514, 1991.

Fekete et al., "Synthesis of octa- and dodecamers of D-ribitol-1-phosphate and their protein conjugates," *Carbohydrate Research* 341(12):2037-2048, Sep. 2006.

Jennings et al., "Conjugation of Meningococcal Lipopolysaccharide R-Type Oligosaccharides to Tetanus Toxoid as Route to a Potential Vaccine Against Group B *Neisseria meningitidis*," *Infection and Immunity* 43(1):407-412, Jan. 1984.

Kubler-Kielb et al., "A New Method for Conjugation of Carbohydrates to Proteins Using an Aminooxy-Thiol Heterobifunctional Linker," *J. Org. Chem.* 70(17):6987-6990, 2005.

Kubler-Kielb et al., "Immunochemical Characterization of Lipopolysaccharides of *B. parapertussis* and *B. bronchiseptica* for Preparation of Glycoconjugate Vaccine against Kennel Cough in Dogs and Coughing Disease in Humans," *Abstract for XXIIIrd International Carbohydrate Symposium*, Jul. 23-28, 2006, Whistler, Canada and Satellite Meeting "Resent Advances in Synthetic Carbohydrate Chemistry," Jul. 22, 2006, Vancouver, Canada.

Langenhan et al., "Recent Carbohydrate-Based Chemoselective Ligation Applications," *Current Organic Synthesis* 2(1):59-81, 2005.

Lees et al., "Versatile and efficient synthesis of protein-polysaccharide conjugate vaccines using aminooxy reagents and oxime chemistry," *Vaccine* 24:716-729, 2006.

Melaugh et al., "Partial Characterization of the Major Lipooligosaccharide from a Strain of *Haemophilus ducreyi*, the Causative Agent of Chancroid, a Genital Ulcer Disease," *The Journal of Biological Chemistry* 267(19):13434-13439, Jul. 1992.

Pozsgay et al., "Effect of the nonreducing end of *Shigella dysenteriae* type 1 O-specific oligosaccharides on their immunogenicity as conjugates in mice," *PNAS* 104(36):14478-14482, Sep. 2007.

Roy et al., "Improved procedures for the conjugation of oligosaccharides to protein by reductive amination," *Can. J. Biochem. Cell Biol.* 62:270-275, 1984.

Rybka et al., "Determination of endotoxin by the measurement of the acetylated methyl glycoside derivative of Kdo with gas-liquid chromatography-mass spectrometry," *Journal of Microbiological Methods* 64:171-184, 2006 (available online Jun. 1, 2005).

Schwartz et al., "Proteins Containing Reductively Aminated Disaccharides," *Archives of Biochemistry and Biophysics* 181:542-549, 1977.

Schweda et al., "Structural Studies of the Cell Envelope Lipopolysaccharides from *Haemophilus ducreyi* Strains ITM 2665 and ITM 4747," *The Journal of Biological Chemistry* 269(16):12040-12048, Apr. 1994.

International Search Report dated Feb. 12, 2008 from International Application No. PCT/US2007/016373.

* cited by examiner

METHODS FOR CONJUGATION OF OLIGOSACCHARIDES OR POLYSACCHARIDES TO PROTEIN CARRIERS THROUGH OXIME LINKAGES VIA 3-DEOXY-D-MANNO-OCTULSONIC ACID

CROSS REFERENCE TO RELATED APPLICATIONS

This is the U.S. National Stage of International Application No. PCT/USUS2007/016373, filed Jul. 18, 2007, which was published in English under PCT Article 21(2), which in turn claims the benefit of U.S. Provisional Application No. 60/832,448, filed Jul. 21, 2006. Both applications are incorporated herein in their entirety.

FIELD

Disclosed herein are conjugates and methods for making conjugates from oligosaccharide or polysaccharide antigens.

BACKGROUND

There are numerous human and animal diseases or infections that can be caused by Gram-negative bacteria such as, for example, *Bordetella* spp. and *Haemophilus ducreyi*.

Vaccination has proven effective for preventing infection of humans and animals by *Bordetella* spp. Killed whole cell and subunit vaccines have been used to immunize parenterally to protect humans against *pertussis* caused by *Bordetella pertussis*, a highly contagious, severe respiratory infection especially of young children. *B. parapertussis* causes a milder and less frequent form of the disease, but its incidence and importance is garnering increasing attention. No vaccine is known to prevent it. Vaccination against *B. pertussis* does not protect against *B. parapertussis*. *Parapertussis* infection followed by pertussis in the same individuals has been described in literature. *B. pertussis* is confined to human, while *B. parapertussis* is confined to human and sheep. *B. bronchiseptica* causes respiratory infections in a variety of hosts: kennel cough in dogs, atrophic rhinitis in piglets, bronchopneumonia in rabbits and guinea pigs. Rarely, it infects humans, but young children, animal handlers and increasingly immuno-compromised individuals are susceptible. Unlike most bacterial respiratory pathogens, *B. bronchiseptica* efficiently colonizes the ciliated epithelium of the respiratory tract of the host and may establish chronic infections. A cellular veterinary vaccine is available but it is of limited efficacy.

It has been shown that protection to the infections caused by gram-negative bacteria can be conferred by serum anti-lipopolysaccharide (LPS) IgG. Cohen et al., "Double-blind vaccine-controlled randomised efficacy trial of an investigational *Shigella sonnei* conjugate vaccine in young adults," *Lancet* 349(9046):155-159, 1997. The LPSes of all three bordetellae share several similar features, though none of them is identical in structure. *B. pertussis* produce rough-type LPS comprising a Lipid A domain and branched dodecasaccharide chain, carrying unusual sugars and free amino and carboxylic groups. On the basis of SDS-PAGE migration, it is divided into Band B—Lipid A and a branched nanosaccharide, that if further substituted by a trisaccharide unit is termed Band A. Almost identical core structure was reported for *B. bronchiseptica* LPS. On the contrary, *B. parapertussis* core region has a simplified heptasaccharide structure; it does not contain Band A trisaccharide and Band B lacks one heptose and one N-acetylgalactosamine substituents. Only *B. bronchiseptica* and *B. parapertussis* synthesize O-specific polysaccharides (O-SP) and initially it was reported that they carry identical structure of linear polymers of 1,4-linked 2,3-diacetamido-2,3-dideoxy-α-galactouronic acid (Di Fabio J L et al., *FEMS Microbiol. Lett* 97:275-282, 1992). However later, serological differences between *B. bronchiseptica* strains were observed and ascribed to the structural variations of the non-reducing end-groups of LPS O-chains (Vinogradov E. et al., *Eur. J. Biochem.* 276:7230-7236, 2000). As it was reported for *Vibrio cholerae* O1 serotype Ogawa and Inaba, the non-reducing end-groups play a significant role as major epitopes in serological reactions (Wang J., *J. Biol. Chem.* 273:2777-2783, 1998). Similar observation was made in case of *Salmonella* O40 and O43 serotypes.

Chancroid is a sexually transmitted genital ulcer disease (GUD) caused by the bacterium *Haemophilus ducreyi*. Chancroid presents with characteristic and persistent genital ulcers on the external genitals, associated with regional lymphadenopathy in 50% of cases. The disease is common in many developing countries, and is considered a significant risk factor together with other genital GUD, e.g. herpes simplex virus 2 (HSV-2) for heterosexual HIV transmission in geographic areas where both diseases are prominent.

A number of putative virulence factors of *H. ducreyi* have been described which may play a role in pathogenicity of this organism. Two of these factors are toxins: a hemolytic toxin and cytolethal distending toxin. The outer membrane proteins, DsrA and DltA, have been shown to promote resistance to killing by normal human serum. The hemoglobin receptor HgbA and the Cu, Zn-superoxide dismutase both seem to play a role in iron acquisition for *H. ducreyi*. Filamentous hemagglutinin like protein is involved in inhibition of phagocytosis. Heat-shock proteins (HSP) of *H. ducreyi* situated on the surface of the bacteria are responsible for protection of these bacteria against changes in the environment and enhance *H. ducreyi* adhesion to mammalian cells. Additionally, a number of proteins have been shown to play a role in adherence.

The lipooligosaccharide (LOS) produced by *H. ducreyi* is a putative virulence facto, as well. Previous studies have shown that LOS plays a role in adherence of bacteria to keratinocytes and human foreskin fibroblasts and also contribute to the development of lesions in animal models. Structural studies have been performed on the LOS from a number of *H. ducreyi* strains, e.g. 35000, ITMA 2665, 3147, 5535, CCUG 7470, 4438 and others. These studies have shown that the predominant form of the core oligosaccharide of the LOS is composed of 10 saccharides with a lactosamine or sialyllactosamine at the non-reducing end and is expressed by majority of strains.

*H. ducreyi* enters the skin or mucosa through wounds and attaches to extracellular matrix and to cells. This stimulates an inflammatory response with the development of pro-inflammatory cytokines and assembly of phagocytic cells; granulocytes and macrophages, at the infection site. *H. ducreyi* may be found both intra and extracellularly. The inflammatory process may clear the organism partially but may also cause tissue destruction and chronic infection with granuloma formation as observed in rabbit model of infection.

The mediators of immunity to chancroid are not known. Data from patients and infected volunteers indicate that this local infection does not confer immunity against subsequent re-infection and do not induce an antibody response. The results from these experiments indicate that the cytokine pattern and the type of cells involved in the early immune response to *H. ducreyi*, may have features of a Th1 response, including a poor or no antibody response. The in vitro studies of interactions of *H. ducreyi* with human monocyte-derived-dendritic cells and with macrophages confirmed an initial Th1 response. Studies in a rabbit model showed that both antibodies and cellular immunity contributed to reducing the number of bacteria in the lesions, thus contributing to protection. Data from a swine model indicated that antibodies alone, at levels achieved only after more than 3 injections of live bacteria, are sufficient for protection. Antibodies to different bacterial cell components were detected in the late stage of disease in sera from patients with chancroid, but antibodies neutralizing CDT have been detected only in about 28% of chancroid cases. It has also been noted that antibodies specific to the LOS of this organism enhance opsonophagocytic killing of *H. ducreyi* in vitro, but such antibodies are not elicited in sufficient amounts after repeated dermal injections of bacteria to animals. Low level of induced LOS antibodies may be due to the fact that the LOS structure resembles terminal saccharides of paraglobise, a major antigen on human erythrocytes and muscles. Since re-infection with *H. ducreyi* can occur, the immunity, including the amount and specificity of antibodies elicited by this local infection, is likely not sufficient for protection.

The covalent binding of oligosaccharide to carrier proteins by random activation of the saccharide using CDAP and ADH as the linker, resulted in conjugates that induced higher levels of IgG anti LOS than repeated injections of the whole cell (Lundquist A, Ahlman k T. Lagergärd, "Preparation and immunological properties of *Haemophilus ducreyi* lipooligosaccharide-protein conjugates," ASM Meeting, abstract e-044, New Orleans, 2004). A vaccine to prevent chancroid would reduce/prevent the disease burden and have the added benefit of reducing HIV incidence.

Shigellae are Gram-negative bacteria, pathogens to humans only, that can cause endemic and epidemic dysentery worldwide, especially in the developing countries. The symptoms usually start with watery diarrhea that later develops into dysentery, characterized by high fever, blood and mucus in the stool, and cramps. *Shigella flexneri* causes dysentery mostly in developing countries with more fatalities then any other *Shigella* species. The disease can be prevented by vaccination using the polysaccharide part of the LPS as an immunogen.

SUMMARY

Disclosed herein are methods for preparing an oligosaccharide-protein carrier immunogenic conjugate or a polysaccharide-protein carrier immunogenic conjugate. The methods include:

obtaining an oligosaccharide or polysaccharide having an anhydro 3-deoxy-D-manno-octulsonic acid moiety located at the terminal reducing end of the oligosaccharide or polysaccharide that includes a carbonyl functional group; and reacting the carbonyl functional group of the anhydro 3-deoxy-D-manno-octulsonic acid moiety with an aminooxylated protein carrier molecule resulting in an oligosaccharide-protein carrier immunogenic conjugate or polysaccharide-protein carrier immunogenic conjugate that includes a covalent oxime bond between the oligosaccharide and the protein carrier or the polysaccharide and the protein carrier.

Also described herein are immunogenic conjugates comprising the structure of:

Pr-Sp-O—N═C(COOH)-anh-KDO—OS wherein Pr is a carrier protein, Sp is an optional spacer moiety, anh-KDO is an anhydro moiety from 3-deoxy-D-manno-octulsonic acid, and OS is an oligosaccharide or polysaccharide residue from the cleavage of Lipid A from a lipopolysaccharide.

Further disclosed are methods of eliciting an immune response in a subject, comprising administering to the subject the above-described conjugates, thereby eliciting an immune response in the subject.

Another embodiment for preparing an oligosaccharide-protein carrier immunogenic conjugate or polysaccharide-protein carrier immunogenic conjugate includes obtaining an oligosaccharide or polysaccharide having an anhydro 3-deoxy-D-manno-octulsonic acid moiety located at the terminal reducing end of the oligosaccharide or polysaccharide. The anhydro 3-deoxy-D-manno-octulsonic acid moiety of the oligosaccharide or polysaccharide is reacted with a heterobifunctional compound that includes at least one aminooxy group. Subsequently, the resulting functionalized oligosaccharide or polysaccharide is reacted with a protein carrier to produce an oligosaccharide-protein carrier immunogenic conjugate or polysaccharide-protein carrier immunogenic conjugate that includes a covalent oxime bond between the oligosaccharide and the protein carrier or the polysaccharide and the protein carrier.

The foregoing and other features and advantages will become more apparent from the following detailed description, which proceeds with reference to the accompanying figures.

BRIEF DESCRIPTION OF TILE DRAWINGS

FIG. 1 is a conjugation reaction scheme that depicts (a) the synthesis of aminooxylated protein, (b) the synthesis of an oligosaccharide or polysaccharide that includes a carbonyl functional group (i.e, ketone), and (c) the conjugation of the aminooxylated protein with the carbonyl-functional oligosaccharide or polysaccharide. Pr is a carrier protein, LPS is lipopolysaccharide, LOS is a lipooligosaccharide, O-chain is an O-antigen oligosaccharide or polysaccharide chain, Core is a core oligosaccharide or polysaccharide chain, KDO4P is 3-deoxy-D-manno-octulsonic acid moiety phosphorylated at position C4, and anhydro-KDO is described below.

FIG. 2 is a LPS structure of *Bordetella parapertussis* and *Bordetella bronchiseptica*. A novel pentasaccharide (-4-β-ManNAc3ANcAN-4-β-GlcNAc3NAcAN-4-α-GalNAc-4-β-ManNAc3NAcA-3-β-FucNAc4NMe-) present between the O-SP and the core was identified. In addition, besides the reported structure the O-SP of *B. bronchiseptica* and *B. parapertussis* being a homopolymer of 1,4-linked 2,3-diacetamido-2,3-dideoxy-α-galacturonic acid, it was found that both O-SP contain amidated uronic acids, the number of which varied between strains (Preston et al., *J. Biol. Chem.*, 2006 (in press)). Certain fragments (-6-β-GlcNAc-4-β-ManNAc3NAcA-3-β-FucNAc4NMe-) are not present or partially present (residues with *) in *B. parapertussis*. Two types of O-SP end groups (Vinogradov et al., *Eur. J. Biochem.* 267:7230-7237, 2000) (A) were found in *B. bronchiseptica* and only one, Ala-type, in *B. parapertussis*.

Figure 8:
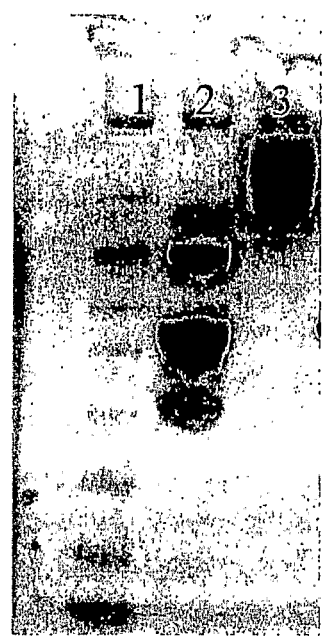

FIG. 8 is an SDS-PAGE gel result showing an increase in molecular size of BSA-ONH$_2$/*S. flexnerii* 2a O-SP conjugate (line 3) over BSA-ONH$_2$ (line 2). Line 1 is a marker. 10% NUPAGE MES gel was used in this experiment. The highest marker line corresponds to 188 kDa.

DETAILED DESCRIPTION

I. Abbreviations

ADH: adipic acid dihydrazide
AT: anthrax toxin

ATR: anthrax toxin receptor
EDAC: 1-ethyl-3-(3-dimethylaminopropyl)carbodiimide-HCl
EF: edema factor
GLC-MS: gas-liquid chromatography-mass spectrometry
kDa: kilodaltons
LC-MS: liquid chromatography-mass spectrometry
LeTx: lethal toxin
LF: lethal factor
LOS: lipooligosaccharide
LPS: lipopolysaccharide
MALDI-TOF: matrix-assisted laser desorption ionization time-of-flight
OS: oligosaccharide
μg: microgram
μl: microliter
PA: protective antigen
PBS: phosphate buffered saline
SBAP: succinimidyl 3-(bromoacetamido) propionate
SFB: succinimidylformylbenzoate
SPDP: N-hydroxysuccinimide ester of 3-(2-pyridyl dithio)-propionic acid
SLV: succinimidyllevulinate
TT: tetanus toxoid The saccharide units disclosed herein are abbreviated as below following conventional oligosaccharide/polysaccharide nomenclature:
anhKDO: anhydro KDO
Fuc: fucose
Gal: galactose
Glc: glucose,
GlcNAc: N-acetylglucosamine
GalNAc: N-acetylgalactosamine
Hep: glycero-D-manno-heptopyranoside (heptose)
Hex: hexose
Man: mannose
NeuNAc: N-acetylneuramic acid II. Terms Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew a al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all nucleotide sizes or amino acid sizes, and all molecular weight or molecular mass values, given for nucleic acids or polypeptides or other compounds are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various examples of this disclosure, the following explanations of specific terms are provided:

Adjuvant: A substance that non-specifically enhances the immune response to an antigen. Development of vaccine adjuvants for use in humans is reviewed in Singh et al. (*Nat. Biotechnol.* 17:1075-1081, 1999), which discloses that, at the time of its publication, aluminum salts, such as aluminum hydroxide (Amphogel, Wyeth Laboratories, Madison, N.J.), and the MF59 microemulsion are the only vaccine adjuvants approved for human use. An aluminum hydrogel (available from Brentg Biosector, Copenhagen, Denmark, is another common adjuvant).

In one embodiment, an adjuvant includes a DNA motif that stimulates immune activation, for example the innate immune response or the adaptive immune response by T-cells, B-cells, monocytes, dendritic cells, and natural killer cells. Specific, non-limiting examples of a DNA motif that stimulates immune activation include CpG oligodeoxynucleotides, as described in U.S. Pat. Nos. 6,194,388; 6,207,646; 6,214,806; 6,218,371; 6,239,116; 6,339,068; 6,406,705; and 6,429,199.

Analog, Derivative or Mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

Antibodies for use in the methods and devices of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antigen: A compound, composition, or substance that may be specifically bound by the products of specific humoral or cellular immunity, such as an antibody molecule or T-cell receptor. Antigens can be any type of biologic molecule including, for example, simple intermediary metabolites, sugars (e.g., oligosaccharides), lipids, and hormones as well as macromolecules such as complex carbohydrates (e.g., polysaccharides), phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens. In one example, an antigen is a lipopolysaccharide antigen.

Carrier: An immunogenic molecule to which an antigen such as an oligosaccharide or polysaccharide can be bound. When bound to a carrier, the bound molecule may become more immunogenic. Carriers are chosen to increase the immunogenicity of the bound molecule and/or to elicit antibodies against the carrier which are diagnostically, analytically, and/or therapeutically beneficial. Covalent linking of a molecule to a carrier confers enhanced immunogenicity and T-cell dependence (Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, proteins from bacteria or viruses), semi-synthetic or synthetic materials containing one or more functional groups to which a reactant moiety can be attached.

Examples of bacterial products for use as carriers include bacterial toxins, such as *B. anthracis* PA (including fragments that contain at least one antigenic epitope and analogs or derivatives capable of eliciting an immune response), LF and LeTx, and other bacterial toxins and toxoids, such as tetanus toxin/toxoid, diphtheria toxin/toxoid, *P. aeruginosa* exotoxin/toxoid/, pertussis toxin/toxoid, and *C. perfringens* exotoxin/toxoid. Viral proteins, such as hepatitis B surface antigen and core antigen can also be used as carriers.

Covalent Bond: An interatomic bond between two atoms, characterized by the sharing of one or more pairs of electrons by the atoms. The terms "covalently bound" or "covalently linked" refer to making two separate molecules into one contiguous molecule. The terms include reference to joining a hapten or antigen indirectly to a carrier molecule, with an intervening linker molecule.

Epitope: An antigenic determinant. These are particular chemical groups or contiguous or non-contiguous peptide sequences or saccharide units on a molecule that are antigenic, that is, that elicit a specific immune response. An antibody binds a particular antigenic epitope based on the three dimensional structure of the antibody and the matching (or cognate) epitope.

Immune Response: A response of a cell of the immune system, such as a B-cell, T-cell, macrophage or polymorphonucleocyte, to a stimulus. An immune response can include any cell of the body involved in a host defense response, for example, an epithelial cell that secretes interferon or a cytokine. An immune response includes, but is not limited to, an innate immune response or inflammation.

Immunogenic Conjugate or Composition: A term used herein to mean a composition useful for stimulating or eliciting a specific immune response (or immunogenic response) in a vertebrate. In some embodiments, the immunogenic response is protective or provides protective immunity, in that it enables the vertebrate animal to better resist infection or disease progression from the organism against which the immunogenic composition is directed. One specific example of a type of immunogenic composition is a vaccine.

Immunogen: A compound, composition, or substance which is capable, under appropriate conditions, of stimulating the production of antibodies or a T-cell response in an animal, including compositions that are injected or absorbed into an animal.

Immunologically Effective Dose: An immunologically effective dose of the oligosaccharide-protein or polysaccharide-protein conjugates of the disclosure is therapeutically effective and will prevent, treat, lessen, or attenuate the severity, extent or duration of a disease or condition, for example, infection by *Bordetella parapertussis* or *Bordetella bronchiseptica.*

Inhibiting or Treating a Disease: inhibiting the full development of a disease or condition, for example, in a subject who is at risk for a disease such as respiratory tract infections. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated: An "isolated" biological component (such as a lipopolysaccharide) has been substantially separated or purified away from other biological components in the cell of the organism in which the component naturally occurs, such as other chromosomal and extra-chromosomal DNA and RNA, proteins, glycolipids and organelles.

Lipopolysaccharide (LPS): LPS is an endotoxin that is a major suprastructure of the outer membrane of Gram-negative bacteria which contributes greatly to the structural integrity of the bacteria, and protects them from host immune defenses. LPS typically contains three components: (a) Lipid A (a hydrophobic domain that typically consists of a glucosamine disaccharide that is substituted with phosphate groups and long chain fatty acids in ester and amide linkages); (b) a core polysaccharide or oligosaccharide that can include, for example, heptose, glucose, galactose and N-acetylglucosamine units depending upon the genera and species of bacteria; and (c) optionally, polysaccharide distal or side chain(s) (often referred to as the "0 antigen" that can include, for example, mannose, galactose, D-glucose, N-acetylgalactosamine, N-acetylglucosamine, L-rhamnose, and a dideoxyhexose depending upon the genera and species of bacteria). Lipid A and the core polysaccharide or oligosaccharide domains are joined together by one or more units of 3-deoxy-D-manno-octulsonic acid ("KDO", also known as ketodeoxyoctonate). A lipooligosaccharide (LOS) (also known as a "short chain LPS") commonly refers to an LPS that contains Lipid A plus a core polysaccharide or oligosaccharide (e.g., in *H. ducreyi* and *B. pertussis* that does not naturally contain any 0 antigen chains). As used herein, the term LPS can include short chain LPS and LOS.

Oligosaccharide (OS): As used herein, the term "oligosaccharide" is not necessarily restricted to a molecule having a specific number of saccharide units. However, in general, an oligosaccharide is a carbohydrate that contains from about 3 to about 10 simple sugars (e.g., monosaccharides) linked together. O-specific oligosaccharide (O-SP) refers to an O-specific oligosaccharide chain attached to a core oligosaccharide or polysaccharide chain. The oligosaccharides or polysaccharides conjugated to the protein carrier do not include a lipid component.

Pharmaceutically Acceptable Carriers: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more SARS-CoV nucleic acid molecules, proteins or antibodies that bind these proteins, and additional pharmaceutical agents. The term "pharmaceutically acceptable carrier" should be distinguished from "carrier" as described above in connection with a hapten/carrier conjugate or an antigen/carrier conjugate.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Protein: A molecule, particularly a polypeptide, comprised of amino acids.

Purified: The term "purified" does not require absolute purity; rather, it is intended as a relative term. Thus, for example, a purified peptide, protein, conjugate, LPS, or other active compound is one that is isolated in whole or in part from proteins, lipids or other contaminants. Generally, substantially purified peptides, proteins, conjugates, LPSs or other active compounds for use within the disclosure comprise more than 80% of all macromolecular species present in a preparation prior to admixture or formulation of the peptide, protein, conjugate, LPS or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, conjugate, LPS or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

Therapeutically Effective Amount: A quantity of a specified agent sufficient to achieve a desired effect in a subject being treated with that agent. For example, this may be the amount of an OS-protein or polysaccharide-protein conjugate useful in increasing resistance to, preventing, ameliorating, and/or treating infection and disease caused by *Bordetella parapertussis, Bordetella bronchiseptica, Haemophilus ducreyi, Bordetella pertussis, Vibrio cholere*, or *Haemophilus influenza* infection in a subject. Ideally, a therapeutically effective amount of an agent is an amount sufficient to increase resistance to, prevent, ameliorate, and/or treat infection and disease caused by *Bordetella parapertussis, Bordetella bronchiseptica, Haemophilus ducreyi, Bordetella pertussis, Vibrio cholere*, or *Haemophilus influenza* infection in a subject without causing a substantial cytotoxic effect in the subject. The effective amount of an agent useful for increasing resistance to, preventing, ameliorating, and/or treating infection and disease caused by *Bordetella parapertussis, Bordetella bronchiseptica, Haemophilus ducreyi, Bordetella pertussis, Vibrio cholere*, or *Haemophilus influenza* infection in a subject will be dependent on the subject being treated, the severity of the affliction, and the manner of administration of the therapeutic composition.

Toxoid: A nontoxic derivative of a bacterial exotoxin produced, for example, by formaldehyde or other chemical treatment. Toxoids are useful in the formulation of immunogenic compositions because they retain most of the antigenic properties of the toxins from which they were derived.

Vaccine: A vaccine is a pharmaceutical composition that elicits a prophylactic or therapeutic immune response in a subject. In some cases, the immune response is a protective response. Typically, a vaccine elicits an antigen-specific immune response to an antigen of a pathogen, for example, a bacterial or viral pathogen, or to a cellular constituent correlated with a pathological condition. A vaccine may include a polynucleotide, a peptide or polypeptide, a polysaccharide, a virus, a bacteria, a cell or one or more cellular constituents. In some cases, the virus, bacteria or cell may be inactivated or attenuated to prevent or reduce the likelihood of infection, while maintaining the immunogenicity of the vaccine constituent.

As described above, disclosed herein are methods for conjugating oligosaccharides or polysaccharides having a 3-deoxy-D-manno-octulsonic acid moiety located at the terminal reducing end of the oligosaccharides or polysaccharides. According to the methods, binding the OS by KDO at the reducing end of the OS means that all of the conserved OS structure remains intact or unmodified (e.g., none of the saccharide residues are oxidized) which provides more potential sites for interaction leading to higher immunogenicity. The conjugates disclosed herein preserve the external non-reducing end of the OS, are recognized by antisera, and induce immune responses in mice.

The oligosaccharide may be obtained from gram-negative bacteria such as *Haemophilus ducreyi, Bordetella bronchiseptica, Bordetella parapertussis, Bordetella pertussis, Vibrio cholere*, or *Haemophilus influenza* or any other *Haemophilus* spp. These bacteria typically contain a lipopolysaccharide (LPS) with a 3-deoxy-D-manno-octulsonic acid moiety phosphorylated at position C4 on the 3-deoxy-D-manno-octulsonic acid moiety.

Also disclosed herein are novel techniques for binding *S. flexnerii* O-SP to protein carrier via KDO. This technique can be applied to other Shigellae like *S. dysenteriae* and *S. sonnei*, as well as to other enterobacteriacea and other gram-negative bacteria having KDO molecule between Lipid A and oligo/polysaccharide chain of their LPS.

The target oligosaccharides or polysaccharides for conjugation typically are those that carry epitopes in their structure. Examples of such oligosaccharides or polysaccharides are described below in more detail in examples 1 and 2. The oligosaccharides or polysaccharides that are conjugated include a general structure of:

O-chain(if present)-core OS-anhydro-KDO

The anhydro-KDO moiety is the moiety that results after acid hydrolysis treatment of the isolated LOS or LPS as described in more detail below and it has a structure represented by (anhydro-KDO could also be referred to as 4, 8(7)-anhydro derivative of KDO):

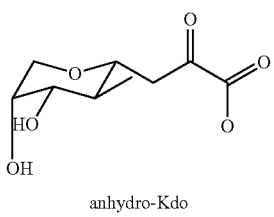

anhydro-Kdo

The oligosaccharide or polysaccharide typically is derived from LPS present in the bacteria identified above. The LPS initially is isolated from the other constituents of the bacteria cell structure. Illustrative LPS-isolation techniques are described, for example, in Westphal et al., *Meth. Carbohydr. Chem.* 5:83-89, 1965, which is incorporated herein by reference in its entirety, and typically involve isolation or purification via a phenol-water extraction. Other LPS-isolation techniques include enzyme digestion and alcohol precipitation, chromatography by gel filtration and ion-exchange.

The isolated LPS then is subjected to mild acid hydrolysis to cleave the Lipid A from the polysaccharide or oligosaccharide domain such that the 3-deoxy-D-manno-octulsonic acid remains linked to the polysaccharide or oligosaccharide domain. Such techniques are described, for example, in Auzanneau, *J. Chem. Soc. Perkin Trans.* 1:509-516, 1991 and Rybka et al., *J. Microblol. Methods* 64(2):171-184, 2006, both of which are incorporated herein by reference. Illustrative hydrolysis conditions include treating the LPS with acetic acid for 1-3 hours at about 100° C., or hydrolyzing LPS in a mixture of acetic acid and sodium acetate (e.g., treating 50 mg LPS with a mixture of 73.5 ml of 0.2 M acetic acid and 26.5 ml of 0.2 M sodium acetate for 5 hours at 100° C. in 5 ml volume). The acid hydrolysis transforms the KDO structure in the isolated LPS to an anhydro-KDO structure.

Conjugation of the oligosaccharide or polysaccharide to the carrier protein is accomplished via formation of an oxime linkage between a carbonyl functional group present in the KDO moiety and an aminooxy functional group present on the carrier protein. The oxime linkage reaction is a chemoselective ligation since it involves the aqueous covalent coupling of unprotected, highly functionalized biomolecules that contain at least a pair of functional groups that react together exclusively, within a biological environment. Oxime linkages can be formed in an aqueous reaction environment, and are stable, from pH 5 to pH 7. Other advantageous features of forming oxime linkages include a relatively short reaction time, a good yield, and formation at ambient temperature. These conditions avoid denaturation of the carrier protein.

The reactive carbonyl functional group present in the KDO moiety can be an aldehyde or a ketone remaining after acid hydrolysis cleavage of the Lipid A from the LPS. The carrier protein is functionalized with an aminooxy group. The synthetic scheme for forming the oxime linkage is shown below:

Pr-Sp-O—NH$_2$+HOOC—C(O)-anh-KDO—OS→Pr-Sp-O—N═C(COOH)-anh-KDO—OS wherein Pr is a carrier protein, Sp is an optional spacer moiety, anh-KDO is anhydro-KDO, and OS is an oligosaccharide or polysaccharide residue from the cleavage of Lipid A from LPS. Condensation between the carbonyl and aminooxy groups leads to a stable oxime linkage between the OS and carrier protein. The spacer moiety may have any structure that is present in the linker reagents as described below. Alternatively, the HOOC—C(O)-anh-KDO—OS structure could be reacted initially with an aminooxy reagent, and the resulting aminooxy-functionalized reactant could be reacted with the protein.

The oxime conjugation reaction is performed at pH 5 to about pH 7 at ambient temperature conditions in an aqueous environment. The reaction time typically ranges from about 8 to about 24 hours. However, less than 100% conjugation completion can be achieved in less than 8 hours, and the 8-24 hour reaction time assumes near 100% conjugation completion.

The carrier protein (or anh-KDO—OS) can be functionalized to include at least one reactive aminooxy moiety by various techniques as described, for example, in Kielb et al., *J. Org. Chem.* 70:6987-6990, 2005 and U.S. Patent Application Publication No. 2005/0169941, both of which are incorporated herein by reference. Functionalization of the carrier protein can result in the inclusion of an optional spacer moiety as noted above. In illustrative examples, a carrier protein (or anh-KDO—OS) may be reacted with a linker reagent to incorporate the spacer moiety and the aminooxy functional moiety. The linker reagent typically is a heterobifunctional compound that includes at least one aminooxy group and a second functional group that is reactive with the carrier protein. Suitable linker reagents include aminooxy-thiol compounds. Illustrative aminooxy-thiol linker reagents include aminoooxy-alkyl-thiols such as (thiolalkyl)hydroxylamines (e.g., O-(3-thiolpropyl)hydroxylamine) and aminooxy-aryl-thiols. In the case of aminooxy-thiol linker reagents, the carrier protein may be treated to introduce thiol-reactive groups. For example, the carrier protein may be treated with a treatment agent that introduces thiol-reactive haloacetamido or thiol-reactive maleimido moieties onto the carrier protein. The haloacetamido-containing protein or maleimido-containing protein is reacted with the aminooxy-thiol reagent to form the aminooxylated carrier protein via the formation of stable thioether linkages.

The amount of oligosaccharide or polysaccharide reacted with the amount of protein may vary depending upon the specific LPS from which the OS is derived and the carrier protein. However, the respective amounts should be sufficient to introduce about 5-20 chains of OS (PS) onto the protein. In certain examples, the mol ratio of carbonyl groups on OS (PS) to aminooxy groups on the protein may range from about 0.3:1 to about 1:3, more particularly 1:1 to about 1:2, and more preferably about 1:1. The resulting number of oligosaccharide chains bound to a single protein carrier molecule may vary depending upon the specific LPS and the carrier protein, but in general, about 5 to about 20, more preferably about 10, OS chains can be bound to each protein carrier molecule. The yield based on the amount of protein ranges from about 70 to about 90% in protein derivatization step and about 70 to about 90% after the conjugation with the OS.

Specific, non-limiting examples of water soluble protein carriers include, but are not limited to, natural, semi-synthetic or synthetic polypeptides or proteins from bacteria or viruses. In one embodiment, bacterial products for use as carriers include bacterial wall proteins and other products (for example, streptococcal or staphylococcal cell walls), and soluble antigens of bacteria. In another embodiment, bacterial products for use as carriers include bacterial toxins. Bacterial toxins include bacterial products that mediate toxic effects, inflammatory responses, stress, shock, chronic sequelae, or mortality in a susceptible host. Specific, non-limiting examples of bacterial toxins include, but are not limited to: *B. anthracis* PA (for example, as encoded by bases 143779 to 146073 of GenBank Accession No. NC 007322, herein incorporated by reference), including variants that share at least 90%, at least 95%, or at least 98% amino acid sequence homology to PA, fragments that contain at least one antigenic epitope, and analogs or derivatives capable of eliciting an immune response; *B. anthracis* LF (for example, as encoded by the complement of bases 149357 to 151786 of GenBank Accession No. NC 007322); bacterial toxins and toxoids, such as tetanus toxin/toxoid (for example, as described in U.S. Pat. Nos. 5,601,826 and 6,696,065); diphtheria toxin/toxoid (for example, as described in U.S. Pat. Nos. 4,709,017 and 6,696,065); *P. aeruginosa* exotoxin/toxoid/(for example, as described in U.S. Pat. Nos. 4,428,931, 4,488,991 and 5,602,095); pertussis toxin/toxoid (for example, as described in U.S. Pat. Nos. 4,997,915, 6,399,076 and 6,696,065); and *C. perfringens* exotoxin/toxoid (for example, as described in U.S. Pat. Nos. 5,817,317 and 6,403, 094). Viral proteins, such as hepatitis B surface antigen (for example, as described in U.S. Pat. Nos. 5,151,023 and 6,013, 264) and core antigen (for example, as described in U.S. Pat. Nos. 4,547,367 and 4,547,368) can also be used as carriers, as well as proteins from higher organisms such as keyhole limpet hemocyanin, horseshoe crab hemocyanin, edestin, mammalian serum albumins, and mammalian immunoglobulins.

Following conjugation of the oligosaccharide or polysaccharide to the carrier protein, the conjugate can be purified by a variety of techniques well known to one of skill in the art. One goal of the purification step is to remove the unbound oligosaccharide or polysaccharide from the conjugation reaction product composition. One method for purification, involving ultrafiltration in the presence of ammonium sulfate, is described in U.S. Pat. No. 6,146,902. Alternatively, the conjugates can be purified away from unreacted oligosaccharide/polysaccharide and carrier by any number of standard techniques including, for example, size exclusion chromatography, density gradient centrifugation, hydrophobic interaction chromatography, or ammonium sulfate fractionation. See, for example, Anderson et al., *J. Immunol.* 137:1181-1186, 1986 and Jennings & Lugowski, *J. Immunol.* 127:1011-1018, 1981. The compositions and purity of the conjugates can be determined by GLC-MS and MALDI-TOF spectrometry.

The conjugates disclosed herein may be included in pharmaceutical compositions (including therapeutic and prophylactic formulations), typically combined together with one or more pharmaceutically acceptable vehicles and, optionally, other therapeutic ingredients (for example, antibiotics or anti-inflammatories).

Such pharmaceutical compositions can be administered to subjects by a variety of mucosal administration modes, including by oral, rectal, intranasal, intrapulmonary, or transdermal delivery, or by topical delivery to other surfaces. Optionally, the conjugate can be administered by non-mucosal routes, including by intramuscular, subcutaneous, intravenous, intra-atrial, intra-articular, intraperitoneal, or parenteral routes. In other alternative embodiments, the conjugate can be administered ex vivo by direct exposure to cells, tissues or organs originating from a subject.

To formulate the pharmaceutical compositions, the conjugate can be combined with various pharmaceutically acceptable additives, as well as a base or vehicle for dispersion of the conjugate. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The conjugate can be dispersed in a base or vehicle, which can include a hydrophilic compound having a capacity to disperse the conjugate, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The conjugate can be combined with the base or vehicle according to a variety of methods, and release of the conjugate can be by diffusion, disintegration of the vehicle, or associated formation of water channels. In some circumstances, the conjugate is dispersed in microcapsules (microspheres) or nanocapsules (nanospheres) prepared from a suitable polymer, for example, isobutyl 2-cyanoacrylate (see, for example, Michael et al. *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the conjugate can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the conjugate can be brought about by including in the composition an agent which delays absorption, for example, monostearate salts and gelatin.

In certain embodiments, the conjugate can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the conjugate and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the conjugate in the required amount in an appropriate solvent with one or a combination of ingredients enumerated herein, as required, followed by filtered sterilization. Generally, dispersions are prepared by incorporating the conjugate and/or other biologically active agent into a sterile vehicle that contains a basic dispersion medium and the required other ingredients from those enumerated herein. In the case of sterile powders, methods of preparation include vacuum drying and freeze-drying which yields a powder of the conjugate plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the conjugate can be delivered to a subject in a manner consistent with conventional methodologies associated with management of the disorder for which treatment or prevention is sought. In accordance with the disclosure herein, a prophylactically or therapeutically effective amount of the conjugate and/or other biologically active agent is administered to a subject in need of such treatment for a time and under conditions sufficient to prevent, inhibit, and/or ameliorate a selected disease or condition or one or more symptom(s) thereof.

Typical subjects intended for treatment with the compositions and methods of the present disclosure include humans, as well as non-human primates and other animals. To identify subjects for prophylaxis or treatment according to the methods of the disclosure, accepted screening methods are employed to determine risk factors associated with a targeted or suspected disease of condition (for example, coughing disease) as discussed herein, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize disease-associated markers. These and other routine methods allow the clinician to select patients in need of therapy using the methods and pharmaceutical compositions of the disclosure. In accordance with these methods and principles, a conjugate and/or other biologically active agent can be administered according to the teachings herein as an independent prophylaxis or treatment program, or as a follow-up, adjunct or coordinate treatment regimen to other treatments, including surgery, vaccination, immunotherapy, hormone treatment, cell, tissue, or organ transplants, and the like.

The conjugates can be used in coordinate vaccination protocols or combinatorial formulations. In certain embodiments, novel combinatorial immunogenic compositions and coordinate immunization protocols employ separate immunogens or formulations, each directed toward eliciting an anti-LPS or an anti-LOS immune response. Separate immunogens that elicit the anti-LPS or anti-LOS immune response can be combined in a polyvalent immunogenic composition administered to a subject in a single immunization step, or they can be administered separately (in monovalent immunogenic compositions) in a coordinate immunization protocol. For example, a combinatorial or a polyvalent immunogenic composition could include (i) an oligosaccharide or polysaccharide obtained from *Bordetella bronchiseptica* or *Bordetella pertussis* as a first component and (ii) oligosaccharide or polysaccharide obtained from *Bordetella parapertussis* as a second component.

The administration of the conjugate of the disclosure can be for either prophylactic or therapeutic purpose. When provided prophylactically, the conjugate is provided in advance of any symptom. The prophylactic administration of the conjugate serves to prevent or ameliorate any subsequent infection. When provided therapeutically, the conjugate is provided at (or shortly after) the onset of a symptom of disease or infection. The conjugate of the disclosure can thus be provided prior to the anticipated exposure to *Haemophilus ducreyi, Bordetella bronchiseptica, Bordetella parapertussis, Bordetella pertussis, Vibrio cholere, Shigella* sp. or *Haemophilus influenza*, so as to attenuate the anticipated severity, duration or extent of an infection and/or associated disease symptoms, after exposure or suspected exposure to the bacteria, or after the actual initiation of an infection.

For prophylactic and therapeutic purposes, the conjugate can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the conjugate can be provided as repeated doses within a prolonged prophylaxis or treatment regimen, that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the conjugate (for example, amounts that are effective to elicit a desired immune response or alleviate one or more symptoms of a targeted disease). In alternative embodiments, an effective amount or effective dose of the conjugate may simply inhibit or enhance one or more selected biological activities correlated with a disease or condition, as set forth herein, for either therapeutic or diagnostic purposes.

The actual dosage of the conjugate will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the conjugate for eliciting the desired activity or biological response in the subject. Dosage regimens can be adjusted to provide an optimum prophylactic or therapeutic response. A therapeutically effective amount is also one in which any toxic or detrimental side effects of the conjugate and/or other biologically active agent is outweighed in clinical terms by therapeutically beneficial effects. A non-limiting range for a therapeutically effective amount of a conjugate and/or other biologically active agent within the methods and formulations of the disclosure is about 0.01 mg/kg body weight to about 10 mg/kg body weight, such as about 0.05 mg/kg to about 5 mg/kg body weight, or about 0.2 mg/kg to about 2 mg/kg body weight.

Upon administration of a conjugate of the disclosure (for example, via injection, aerosol, oral, topical or other route), the immune system of the subject typically responds to the immunogenic composition by producing antibodies specific for LPS, LOS and/or an antigenic epitope presented by the conjugate. Such a response signifies that an immunologically effective dose of the conjugate was delivered. An immunologically effective dosage can be achieved by single or multiple administrations (including, for example, multiple administrations per day), daily, or weekly administrations. For each particular subject, specific dosage regimens can be evaluated and adjusted over time according to the individual need and professional judgment of the person administering or supervising the administration of the conjugate. In some embodiments, the antibody response of a subject administered the compositions of the disclosure will be determined in the context of evaluating effective dosages/immunization protocols. In most instances it will be sufficient to assess the antibody titer in serum or plasma obtained from the subject. Decisions as to whether to administer booster inoculations and/or to change the amount of the composition administered to the individual can be at least partially based on the antibody titer level. The antibody titer level can be based on, for example, an immunobinding assay which measures the concentration of antibodies in the serum which bind to a specific antigen, for example, LPS and/or LOS.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth. To achieve the same serum concentration level, for example, slow-release particles with a release rate of 5 nanomolar (under standard conditions) would be administered at about twice the dosage of particles with a release rate of nanomolar.

The methods of using conjugates, and the related compositions and methods of the disclosure, are useful in increasing resistance to, preventing, ameliorating, and/or treating infection and disease caused by *Bordetella, H. ducreyi, Vibrio cholere, Shigella* sp. or *Haemophilus influenza* in animal hosts, and other, in vitro applications. These immunogenic compositions can be used for active immunization for prevention of infection, and for preparation of immune antibodies. The immunogenic compositions are composed of non-toxic components, suitable for infants, children of all ages, and adults.

The methods of the disclosure are broadly effective for treatment and prevention of bacterial disease and associated inflammatory, autoimmune, toxic (including shock), and chronic and/or lethal sequelae associated with bacterial infection. Therapeutic compositions and methods of the disclosure for prevention or treatment of toxic or lethal effects of bacterial infection are applicable to a wide spectrum of infectious agents. Non-lethal toxicities that will be ameliorated by these methods and compositions can include fatigue syndromes, inflammatory/autoimmune syndromes, hypoadrenal syndromes, weakness, cognitive symptoms and memory loss, mood symptoms, neurological and pain syndromes and endocrine symptoms. Any significant reduction or preventive effect of the conjugate with respect to the foregoing disease condition(s) or symptom(s) administered constitutes a desirable, effective property of the subject composition/method of the disclosure.

The instant disclosure also includes kits, packages and multi-container units containing the herein described pharmaceutical compositions, active ingredients, and/or means for administering the same for use in the prevention and treatment of bacterial diseases and other conditions in mammalian subjects. Kits for diagnostic use are also provided. In one embodiment, these kits include a container or formulation that contains one or more of the conjugates described herein. In one example, this component is formulated in a pharmaceutical preparation for delivery to a subject. The conjugate is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

The subject matter of the present disclosure is further illustrated by the following non-limiting Examples.

Example 1

*Bordetella* Conjugates

Bacteria and Cultivation.

The following strains were obtained from ATCC: *B. bronchiseptica* ATCC 10580, Rb50 (ATCC BAA-588), and *B. parapertussis* ATCC 1589; *B. bronchiseptica* 15374, 3145 and *B. parapertussis* 12822 were obtained from Dr. M. Perry (NRC Canada). Bacteria were grown on Bordet-Genguo (BG) agar plates and then transferred to Stainer-Scholte (S-S) media (Stanier D W, Scholte M J. A simple chemically defined medium for the production of phase I *Bordetella pertussis. J Clin Pathol.* 25:732-733, 1970). Bacteria were harvested, killed by boiling for 1 hour and frozen for LPS extraction.

Oligosaccharides.

LPS was isolated by phenol-water extraction and purified by enzyme treatment and ultracentrifugation as described in Westphal O., Jann K., *Meth. Carbohydr. Chem.* 5:83-89, 1965, which is incorporated herein by reference in its entirety. To isolate O-specific oligosaccharide (O-SP), LPS (100 mg) was treated with 1% acetic acid (10 ml) for 60 minutes at 100° C., ultracentrifuged and the carbohydrate-containing supernatant was fractionated on a BioGel P-4 column (1.0×100 cm) in pyridine/acetic acid/water buffer (4/8/988 ml) monitored with a Knauer differential refractometer. 28 mg of O-SP was eluted in void volume and used for conjugation. Alternatively, LPS was deaminated in the following way: 100 mg of LPS was dissolved in the mixture: 6 ml 30% acetic acid, 6 ml 5% sodium nitrite, 6 ml water. Reaction was carried out in room temperature, 6 hours, on the magnetic stirrer followed by ultracentrifugation. The supernatant was lyophilized and purified on BioGel P-4 column using conditions as above. 23 mg of O-SP$_{deam}$ was eluted in void volume and used for conjugation.

Analytic.

Protein concentration was measured by the method of Lowry (O. H. Lowry et al., *J. Biol. Chem.* 193:265, 1951). SDS-PAGE used 14% gels according to the manufacturer's instructions. Double immunodiffusion was performed in 1.0% agarose gel in PBS.

Spectroscopy.

MALDI-TOF mass spectra of the derivatized carrier proteins and the conjugates were obtained with an OmniFlex MALDI-TOF instrument (Bniker Daltonics) operated in the linear mode. Samples for analysis were desalted and 1 μl was mixed with 20 μl of sinapic acid matrix made in 30% CH$_3$CN and 0.1% trifluoroacetic acid. Next, 1 μl of mixture was dried on the sample stage and placed in the mass spectrometer.

Methods.

NMR spectra were recorded at 30° C. in D$_2$O on a Varian UNITY INOVA 500, 600, or 800 instrument, using acetone as reference for proton (2.225 ppm) and carbon (31.5 ppm) spectra. Varian standard programs COSY, NOESY (mixing time of 400 ms), TOCSY (spinlock time 120 ms), HSQC, and gHMBC (long-range transfer delay 100 ms) were used with digital resolution in F2 dimension <2 Hz/pt. ESI-MS and NMR spectroscopy was used to confirm the structure of bordatellae LPS structure.

Molecular mass obtained from MALDI like 135 kDa is a mass of conjugate, from which is subtracted a mass of aminooxylated protein-like aminooxylated-BSA is 73 kDa; the difference is a mass of oligo(poly) saccharide introduced on protein.

Conjugation.

(1) BSA-ONH$_2$/O-SP.

An aminooxylated bovine serum albumin (BSA) was prepared via a two-step procedure as described in Kielb et al., *J. Org. Chem.* 70:6987-6990, 2005, which is incorporated herein by reference in its entirety. First, the protein was treated with succinimidyl 3-(bromoacetamido)propionate (SBAP) to introduce thiol-reactive bromoacetamido moieties. Next, it was coupled with O-(3-thiolpropyl)hydroxylamine, a heterobifunctional linker, to form the aminooxylated protein through stable thioether linkages (BSA-ONH$_2$). For conjugation with O-SP, BSA-ONH$_2$ (5 mg) was reacted with 10 mg of O-SP in 1.5 ml Buffer A (PBS, 0.1% glycerol, 0.005 M EDTA, pH 7.4), at pH 5.7, for 15 hours. Next, it was purified by Sephadex G100 gel filtration in 0.2 M NaCl as eluant and the void volume fraction characterized by protein and sugar assays, immunodiffusion, SDS-PAGE and MALDI-TOF spectroscopy. Three conjugates were obtained this way and named as BSA-ONH$_2$/Bb10580 (#1), BSA-ONH$_2$/BbRb50 (#2) and BSA-ONH$_2$/Bp15898 (#3).

(2) BSA-ONH$_2$/O-SP$_{deam}$

BSA was derivatized to BSA-ONH$_2$ as above and 5 mg was reacted with 10 mg of O-SP$_{deam}$ using the same condition as above. Next, it was purified by Sephadex G100 gel filtration and assayed as above. The products were named BSA-ONH$_2$/Bb10580$_{deam}$ (#4), BSA-ONH$_2$/BbRb50$_{deam}$ (#5) and BSA-ONH$_2$/Bp15898$_{deam}$ (#6).

Immunization.

5 to 6-weeks-old female NIH Swiss Webster mice were immunized s.c. 3 times at 2 weeks intervals with 2.5 μg O-SP as a conjugate in 0.1 ml PBS and groups of 10 exsanguinated 7 days after the second or third injections. Controls received PBS. Hyperimmune mice sera against *B. bronchiseptica* strains 10580 and Rb50, and against *B. parapertussis* strain 15898 were induced by multiple intraperitroneal immunization of mice with heat killed whole bacterial cells.

Antibodies.

Serum IgG antibodies were measured by ELISA. Nunc Maxisorb plates were coated with *B. bronchiseptica* 10580 LPS, Rb50LPS or *B. parapertussis* 15898 LPS at 5 μg/ml in PBS containing 1% trichloroacetic acid as described in Hardy et al., "Enhanced ELISA sensitivity using TCA for efficient coating of biologically active lipopolysaccharides or lipid A to the solid phase," *J. Immunol Methods* 176(1):111-6, 1994. Concentration and the composition of buffer for coating antigen were determined by checkerboard titration. Plates were blocked with 1% BSA in PBS for hyperimmune sera or 1% HSA in PBS for conjugate-induced sera for 1 hour at room temperature. A MRX Dynatech reader was used. Antibody levels were calculated relative to hyperimmune standard serum diluted 1:20,000 for *B. bronchisepaca* 10580; 1:15,000 for *B. bronchiseptica* Rb50 and 1:10,000 for *B. parapertussis* 15898 and assigned a value of 1000 ELISA units (EU). Results were computed with an ELISA data processing program provided by the Biostatistics and Information Management Branch, CDC.

Inhibition ELISA was done by incubating hyperimmune mice sera, diluted to the concentration that gave an A$_{405}$ absorption of 1.0, with 10 or 50 μg of inhibitor per well, for 1 hour at 37° C. and overnight at 4° C. The assay was then continued as above. Sera with and without inhibitor, at the same dilution, were compared. Percent inhibition was defined as (1-A$_{405}$ adsorbed serum/A$_{405}$ non-adsorbed serum)× 100%.

The results are shown below in Table 1.

TABLE 1

Inhibition ELISA.

| Inhibitor | O-SP end-group | Amidation of second O-SP sugar | % of inhibition of hyperimmune whole cell sera | | |
|---|---|---|---|---|---|
| | | | Anti-Bb10580 | Anti-BbRb50 | Anti-Bp15989 |
| Bb 10580 O-SP | Ala | − | 92 | 2 | 50 |
| Bb 110H O-SP | Ala | − | 96 | 3 | 45 |
| Bb Rb50, O-SP | Lac | − | 0 | 93 | 1 |
| Bb 512 O-SP | Lac | − | 1 | 95 | 3 |
| Bp 15898 O-SP | Ala | + | 42 | 5 | 97 |
| Bp 15311 O-SP | Ala | + | 50 | 3 | 98 |
| H. ducrei O-SP | na | Na | 0 | 0 | 0 |

Plates were coated with B. bronchiseptica 10580 LPS, Rb50 or B. parapertussis 15989, respectively at 5 μg/ml and reacted anti-B. bronchiseptica 10580 hyperimmune mice serum diluted 1:40000, Rb50 1:20000 and anti-B. parapertussis 15989 1:20000. Inhibitors were used at 50 μg/well Results.
Chemical Characterization of LPSes Chemical analysis indicated that strains B. bronchiseptica 10580, 15374 and 5137, as well as strains B. parapertussis 15898 and 12822 belong to the "Ala-type" (terminal non-reducing residue -2,3,4-triamino-2,3,4-trideoxy-alpha-galactouronamide is formylated on position 3 and 4 and has N-formyl-L-alanyl or L-alanyl substituents at N-2), whereas strain B. bronchiseptica Rb50 belongs to the "Lac-type" (the same terminal residue is acetylated on position 2, formylated at position 3 and the amino group at position 4 bears a 2-methoxypropionyl substituent).

Serum Antibodies.

Immunogenicity was checked by injection to mice. The average molecular mass of deaminated O-SP from B. bronchiseptica strain 10580, as assayed by ES-MS, was established as 5108 Da. The number of O-SP chains bound per one BSA was estimated to be 15 in conjugate #4. The average mass of O-SP was calculated on the bases of detailed structural analysis of studies LPSes, as reported elsewhere, was established as average of 6588 Da for conjugate #1, 2 and 3. The number of O-SP chains bound per one BSA was estimated to be 10, 10 and 15, respectively. The result are shown below in Table 2.

A novel pentasaccharide was identified in B. bronchiseptica and B. parapertussis LPS. B. bronchiseptica O-SP differed in their non-reducing end-groups: the "ala-type" and the "lac-type." In contrast, all B. parapertussis strains analyzed belonged to the "ala-type." No cross reaction between the two types of B. Bronchiseptica LPS was observed. Inhibition assays showed that the terminal residues of O-SP are immunodominant. BSA/O-SP conjugates were specific and induced antibodies only to the homologous type of O-SP. Accordingly, and based upon epidemiological data, at least two types of LPS should be included in a vaccine according to a preferred embodiment.

Example 2

Haemophilia ducreyl Conjugates

Bacteria and Cultivation.

Haemophilus ducreyi strains 35000 was obtained from Culture Collection Göteborg University (CCUG 7470). Bacteria were cultivated on chocolate agar plates Grand Lux (GLV-3) (Department of Bacteriology, Sahlgrenska Hospital, Göteborg, Sweden), containing 5% brain heart infusion (BHI) agar, 1% horse blood, 1.5% horse serum, 0.06% yeast autolysate, 0.015% IsoVitalex (BBL) and 3 mg/ml vancomycin. The plated bacteria were incubated at 33° C. for 48 hours in high humidity in an anaerobic jar with Anaerocult C (Merk, Darmstad, Germany) for generation of an oxygen-depleted and $CO_2$ enriched atmosphere. The bacteria were harvested and frozen at −20° C. for LOS extraction.

TABLE 2

Composition and serum GM of IgG anti-B. bronchiseptica and B. parapertussis LPS in mice by conjugates of O-SP and O-SP$_{deam}$ bound to bovine serum albumin (BSA).

| # | Conjugate | Mol. mass[1] [kDa] | Ratio protein/ sugar | Mol O-SP/Mol Protein | ELISA units after 3rd injection Coating antigen | | |
|---|---|---|---|---|---|---|---|
| | | | | | 10580 LPS | Rb50 LPS | 15898 LPS |
| 1 | BSA-ONH$_2$/Bb10580 | 135 | 1:0.9 | 9 | 4.9 | 0.3 | 0.4 |
| 2 | BSA-ONH$_2$/BbRb50 | 137 | 1:0.9 | 9 | 2.4 | 132 | 0.4 |
| 3 | BSA-ONH$_2$/Bp15898 | 165 | 1:1.4 | 14 | 0.3 | 0.3 | 12 |
| 4 | BSA-ONH$_2$/Bb10580$_{deam}$ | 130 | 1:1.0 | 11 | 55 | 0.6 | 4.8 |
| 5 | BSA-ONH$_2$/BbRb50$_{deam}$ | 105 | 1:0.5 | 8 | 0.1 | 3.5 | 0.3 |
| 6 | BSA-ONH$_2$/Bp15898$_{deam}$ | 116 | 1:0.7 | 10 | 0.5 | 0.1 | 15.6 |

Mice (10 per group) were immunized with 2.5 μg of polysaccharide as a conjugate/mouse, injected s.c., 3 times, 2 weeks apart.
[1]Mol mass was assayed by Maldi-tof, Mol mass of BSA-ONH$_2$ was 74.2 kDa
The "Ratio protein/sugar" is the mass ratio of the two components of the final conjugate.
The "Mol O-SP/Mol Protein is the mole ratio of the two components of the final conjugate.

Oligosaccharides.

LOS was isolated by phenol-water extraction and purified by enzyme treatment and ultracentrifugation as described in Westphal et al., Meth. Carbohydr. Chem. 5:83-89, 1965. To isolate oligosaccharide (OS), LOS (100 mg) was treated with 1% acetic acid (10 ml) for 60 minutes at 100° C. and the carbohydrate-containing supernatant was fractionated on a BioGel P-4 column (1.0×100 cm) in 0.05 M pyridine acetate buffer (pH 5.6) and monitored with a Knauer differential refractometer.

Analytic.

Protein concentration was measured by the method of Lowry (Lowry et al., *J. Biol. Chem.* 193:265, 1951), sugar concentration by phenol/$H_2SO_4$ assay (Dubois et al., "Colorimetric method for determination of sugars and related substances," *Anal. Chem.*, 28:350-356, 1956), incorporation of benzaldehyde groups by colorimetric reaction with 2-hydrazinopyride (Solulink protocol), and hydrazide by TNBS assay as reported (Habeeb A F, "Determination of free amino groups in proteins by trinitrobenzenesulfonic acid," *Anal Biochem.* 14(3):328-336, 1966).

Spectroscopy.

Sugars were analyzed according to Sawardeker et al (Sawardeker et al., "Quantitative determination of monosaccharides as their alditol acetates by gas-liquid chromatography," *Analyt. Chem* 37:1602-1604, 1965). A 0.5 mg sample of each polysaccharide was hydrolyzed in 1 ml of 10 M HCl for 30 minutes at 80° C., reduced peracetylated and analyzed by GLC-MS using Hewlett-Packard apparatus, model HP 6890, with a type HP-5 glass capillary column (0.32 mm×30 m) and temperature programming at 8° C./minute, from 125-250° C. in the electron ionization (106 eV) mode. Methylation was performed as described in Ciucanu et al., "A simple and rapid method for the permethylation of carbohydrates," *Carbohydr. Res.* 131:209-217, 1984. Methylated compounds were hydrolyzed, converted to alditol acetates, and analyzed by GLC-MS as above. MALDI-TOF mass spectra were obtained with an OmniFlex MALDI-TOF instrument (Bruker Daltonics) operated in the linear mode. Samples for analysis were desalted and 1 µl was mixed with 20 µl of sinnapinic acid matrix made in 30% $CH_3CN$ and 0.1% trifluoroacetic acid. Next, 1 µl of mixture was dried on the sample stage and placed in the mass spectrometer. ESI-MS spectra were recording on the Agilent Series LC/MSD instrument in the negative ion mode $^1H$, $^{13}C$ and $^{31}P$ NMR spectra were recorded at 300 MHz using Varian spectrometer. Solutions of 5-13 mg of analytats in $D_2O$ (99.96 atom % D) were used, with acetone as an internal reference at 2.225 ppm and 31.0 ppm, for $^1H$ and $^{13}C$ respectively, or 85% $H_3PO_4$ containing 10% $D_2O$ as an external reference for $^{31}P$ at −0.73 ppm.

Conjugation.

Conjugation by Oxime Formation.

Aminooxylated BSA or Tetanus toxoid (TI) was prepared via a two step procedure as described in Kielb et al., *J. Org. Chem.* 70:6987-6990, 2005, which is incorporated herein by reference in its entirety. First, the protein was treated with succinimidyl 3-(bromoacetamido)propionate (SBAP) to introduce thiol-reactive bromoacetamido moieties. Next, it was coupled with O-(3-thiolpropyl)hydroxylamine, a heterobifunctional linker featuring terminal aminooxy and thiol groups, to form the aminooxylated protein through stable thioether linkages (Pr—$ONH_2$). For conjugation with O-SP, Pr—$ONH_2$ (10 mg) was reacted with 10 mg of O-SP in 1.5 ml Buffer A (PBS, 0.1% glycerol, 0.005 M EDTA, pH 7.4), at pH 5.7, for 15 hours. Next, it was purified by Sephadex G100 gel filtration in 0.2 M NaCl as eluant and the void volume fraction characterized by protein and sugar assays, immunodiffusion, SDS-PAGE and MALDI-TOF spectroscopy. Two conjugates were obtained this way and named as BSA-$ONH_2$/OS (#1) and TT-$ONH_2$/OS (#2).

Characterization of *H. ducreyi* Oligosaccharide Epitpopes in the Conjugates by Monoclonal Antibodies.

The maxi-sorp ELISA plates were coated with the conjugates (1-2) in concentration 2 µg/ml of sugar as a conjugate and 10 µg/ml LOS over night. As a negative control BSA (10 µg/ml) was used. Plates were blocked with 1% BSA and the medium (concentrated 5×) containing monolonal antibodies (MAHD6 or MADH7 [v]) was added. Plates were incubated 3 hours, washed and anti-mouse alkaline phosphatase conjugate was added. After further incubation, plates were washed and developed. The absorbance at 403 nm was monitored.

Oxime Formation with Hemiacetal Groups.

D-Glucose (10 mg), D-maltose (10 mg) maltotriose (25 mg), D-glucosamine (10 mg) or N-acetyl-D-mannosamine (10 mg) were reacted with O-(3-thiolpropyl)hydroxylamine (6 mg) in 1 ml $D_2O$ adjusted to pH 5.5 with 30% solution of NaOD at 37° C. for 15 hours. Progress of reaction was monitored by $^1H$ NMR. Maltotriose-SH (30 mg) was separated from linker by passing through BioBel P-2 column in 0.05 M pyridine acetate buffer as above and freeze-dried. Next 30 mg of maltotriose-SH was reacted with bromoacetamido-derivatized BSA (15 mg), prepared as above to form maltotriose-BSA conjugate by thioether linkages. Reaction was done in buffer A, pH 7.4, 3 hours and solution was purified on Sephadex G-100 column as above. Extent of conjugation was evaluated by MALDI-TOF. Molecular mass of bromoacetamido-BSA was 73545 Da, while maltotriose-BSA conjugate was 81673 Da, indicated incorporation of 16 maltotriose molecules per BSA.

Immunization.

5 to 6-weeks-old female NIH Swiss Webster mice were immunized sc 3 times at 2 weeks intervals with 2.5 µg OS or PGA as a conjugate in 0.1 ml PBS and groups of 10 exsanguinated 7 days after the second or third injections. Controls received PBS.

Antibodies.

Serum IgG antibodies were measured by ELISA (Taylor et al., *Infect. Immun.* 61:3678-3687, 1993). Nunc Maxisorb plates were coated with *H. ducreyi* LOS, 10 µg/ml PBS (determined by checkerboard titration). A MRX Dynatech reader was used. The reference serum to O-SP and BSA was a pool of sera obtained from mice immunized 3 times with 5 µg of oligosaccharide as a conjugate BSA-CHO/AH-O-SP (Conj. #3), diluted to 1.2000 in the first well and assigned a value of 1000 ELISA units (EU). The reference serum to TT was a pool of sera obtained from mice immunized 3 times with 5 µg of oligosaccharide as a conjugate TT-NOS/O-SP (Conj. #2), diluted to 1:5000 in the first well and assigned a value of 100 ELISA units (EU). Results were computed with an ELISA data processing program provided by the Biostatistics and Information Management Branch, CDC.

Immunology.

SDS-PAGE and Western-blotting used 14% gels according to the manufacturer's instructions. Double immunodiffusion was performed in 1.0% agarose gel in PBS.

Results

Characterization of LOS and LOS-Derived Oligosaccharides.

Mass spectroscopic and NMR analysis of isolated products confirmed the structure of the sugar chain of *H. ducreyi* strain 35000 LOS. The data were in agreement with the published structure (Melaugh et al., "Structure of the major oligosaccharide from the lipooligosaccharide of *Haemophilus* ducreyi strain 35000 and evidence for additional glycoforms," *Biochemistry* 33(44):13070-13078, 1994) as represented below:

α-NeuAc-(2→3)-β-Gal-(1→4)-β-GlcNAc-(1→3)-β-Gal-(1→4)-α-Hep-(1→6)-β-Glc-α-(1→4)-α-Hep-(1→5)-α-Kdo4P-Lipid A
|
α-Hep-(1→2)-α-Hep-(1→3)┘

The sialilation of non-reducing end was estimated at about 60% by NMR and GLC-MS analysis. Hydrolysis of LOS with 1% acetic acid cleaved O-SP from Lipid A on the KDO residue, removing at the same time all sialic acid residues from non-reducing end. The observed molecular mass of this product, recorded by ESI-MS in negative mode was [M−1]=1675.8, which is in agreement with the structure of Hex$_3$HexNAcHep$_4$-anhydro-Kdo as the O-SP for *H. ducreyi* strain 35000. No phosphate group on KDO was detectable also by $^{31}$P-NMR suggested the beta-elimination of phosphate from KDO as was reported that results in anhydro-KDO groups at the reducing end (Auzanneau et al., "Phosphorylated sugars. Part 27. Synthesis and reactions, in acid medium, of 5-O-substituted methyl 3-deoxy-α-D-manno-oct-2-ulopyranosic acid 4-phosphates," *J. Chem. Soc. Perkin Transl.* 1:509-517, 1991; Vinogradov et al., "The structure of the carbohydrate backbone of the core-lipid-A region of the lipopolysaccharide from *Vibrio cholerae* strain H11 (non-O1)," *Eur J Biochem.* 218(2):543-554, 1993). A reactive ketone group was shown to form during beta elimination of a model compound, 5-O-methyl-KDO-4-phosphate. The ketone group was used for conjugation of the OS to the protein carrier.

Characterization of Conjugates.

Conjugation of O-SP to aminooxylated protein gave a conjugate containing average 15 chains of oligosaccharide per protein (#1 and #2). Protein/sugar ratio was analyzed by colorimetric assays and by increase of molecular mass using MALDI-TOF spectroscopy. Although not bound by any theory, it is believed that the conjugate is formed by the reaction of a ketone group on the terminal KDO molecule with O-alkyl hydroxylamine on the protein.

In order to identify the core structure of the *H. ducreyi* LOS in the conjugates two monoclonal antibodies were used to structurally defined epitopes on the *H. ducreyi* LOS [V]

MAHD6 recognize - DD-Hepp1-6β-D-Glcp-

MAHD7 recognize - Glc-β1-4Hepa1-Kdo(P)
↑1,3
Hepa1-2Hep

Conjugates #1 and 2 showed similar levels of recognition as LOS itself (see Table 3 below).

TABLE 3

Binding (ELISA) of Mabs specific to *H. ducreyi* LOS with OS-protein conjugates. Plates were coated with conjugates and reacted with Mabs.

| Conjugates | Absorbance at 403 nm | |
|---|---|---|
| | Mab MAHD6 | MAHD7 |
| BSA-ONH$_2$/OS | 2.73 | 4.18 |
| TT- ONH$_2$/OS | 1.86 | 3.95 |
| LOS | 1.77 | 3.6 |
| BSA | 0.08 | 0.08 |

Immunology.

The conjugates were injected into mice at a dose of 2.5 or 5 microgram of OS as a conjugate per mouse and the IgG anti-*H. ducreyi* LOS levels were assayed by ELISA. The results are presented in Table 4 below. Negligible levels of anti-LOS antibodies were detected in sera. However, when plates were coated with conjugate #2, high level of antibodies was detected in sera induced by conjugate #1. This means that the conjugates induce antibodies to sugar part of this LOS while it is presented on other carrier protein in ELISA assay. Since carrier proteins are different, the antibodies seem to be induced against either common sugar part or the linker moiety. It indicated that epitopes presented on ELISA plates by coating with LOS is different then by coating with conjugate.

TABLE 4

Composition and serum GM of IgG anti-*H. ducreyi* LOS in mice by conjugates of O-SP bound to bovine serum albumin (BSA), and tetanus toxoid (TT) and by lacto-N-neotetraose and sialyl-lacto-N-neotetraose bound to human serum albumine (HSA).

| # | Conjugate | Mol. mass[1] | Ratio protein/ sugar | Mol OS/Mol Protein | Microgr. Pr/ OS injected | Anti- LOS | Anti- Protein | Ani- conjugate |
|---|---|---|---|---|---|---|---|---|
| 1 | BSA-ONH$_2$/OS | 105 kDa | 2:1 | 18 | 5/2.5 | 2 | 656 | 29 (#2) |
| 2 | TT-ONH$_2$/OS | Nd | 6:1 | 15 | 15/2.5 | 4 | 2297 | 295 (#1) |

Mice (10 per group) were immunized with 2.5 µg of oligosaccharide as a conjugate/mouse and injected s.c., 3 times, 2 weeks apart.
[1]assayed by MALDI-TOF The *H. ducreyi* OS/protein conjugate had limited immunogenicity in mice.

Example 3

B. pertussis and B. bronchiseptica Conjugates

Methods:

Bacteria and Cultivation.

B. pertussis ATCC BAA-589 (Tohama I) and B. bronchiseptica ATCC 10580 were grown on Bordet-Gengou (BG) agar plates and transferred to Stainer-Scholte (S-S) media. Bacteria were harvested and killed with 1% formalin.

Oligosaccharides.

LPS was isolated by hot phenol-water extraction and purified by enzyme treatment and ultracentrifugation. To isolate core oligosaccharide (OS), LPS was treated with 1% acetic acid at 10 mg/ml for 60 min at 100° C., ultracentrifuged and the carbohydrate-containing supernatant fractionated on a 1.0×100 cm column of BioGel P-4 in pyridine/acetic acid/water buffer (4/8/988 ml) monitored with a Knauer differential refractometer.

Conjugation.

BSA-ONH$_2$/OS. Bovine serum albumin (BSA, Sigma, St. Louis, Mo.) was derivatized to aminooxylated derivatives in a two step procedure as described in Kielb et al., J. Org. Chem. 70:6987-6990, 2005, which is incorporated herein by reference in its entirety: (1) BSA was treated with succinimidyl 3-(bromoacetamido)propionate (SBAP, Pierce, Pittsburgh, Pa.) to introduce thiol-reactive bromoacetamido moieties (BSA-Br); (2) BSA-Br was coupled with O-(3-thiopropyl) hydroxylamine, a heterobifunctional linker, to form the aminooxylated protein through stable thioether linkages (BSA-ONH$_2$). For conjugation with OS, BSA-ONH$_2$ (5 mg) was reacted with 7 mg of OS in 1.5 ml Buffer A (PBS, 0.1% glycerol, 5 mM EDTA), at pH 5.7, for 15 hours. Next, it was passed through a 1×100 cm Sephadex G-50 column in 0.2 M NaCl as eluent and the void volume fraction characterized by protein assay, immunodiffusion, SDS-PAGE and MALDI-TOF spectroscopy. The obtained conjugates were named BSA-ONH$_2$/Bp (#1), BSA-ONH$_2$/B. b-core (#2)

Immunization was performed as described above in Example 1.

Results:

Oligosaccharides:

B. pertussis LPS contains only a core region composed of 12 sugars:

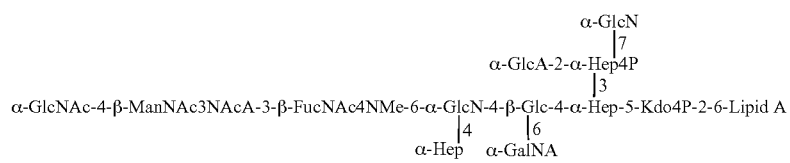

Figure 1:
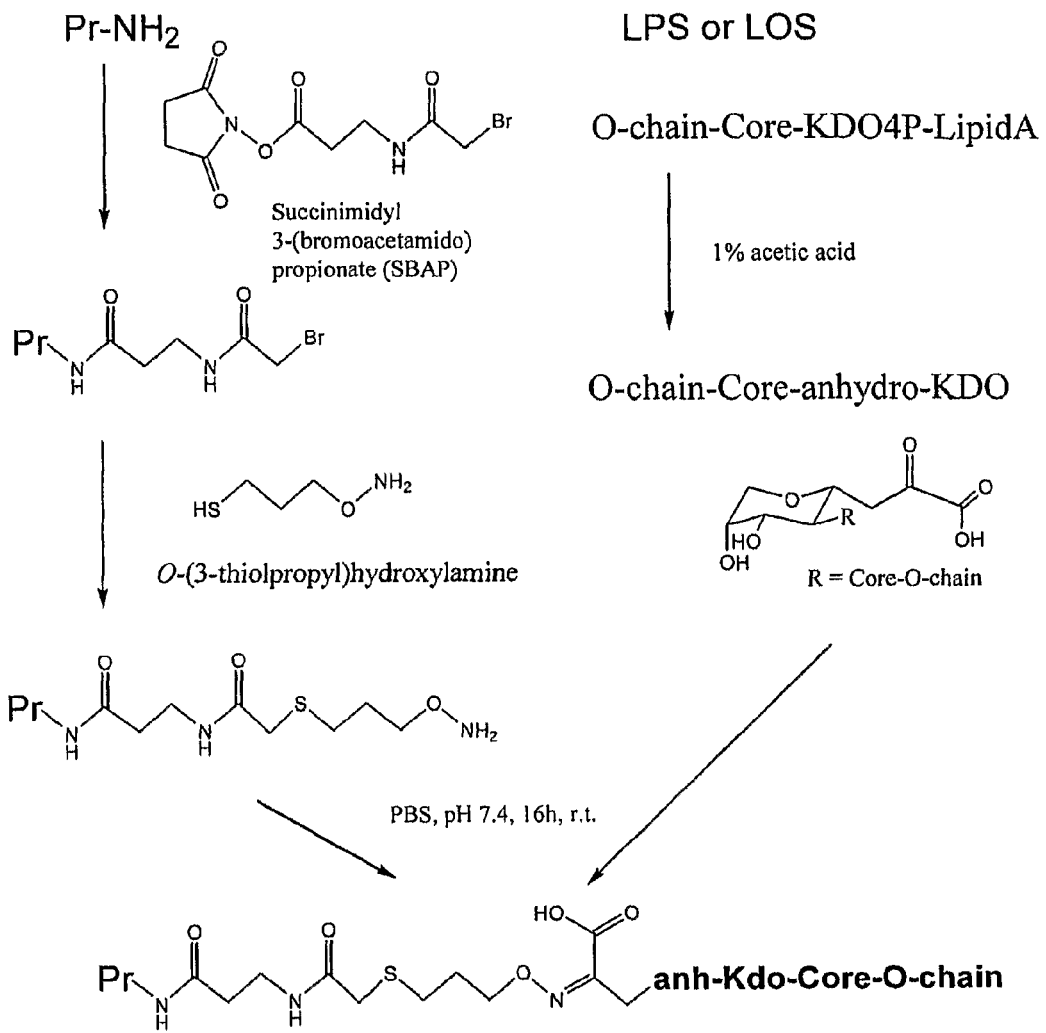
Figure 2:
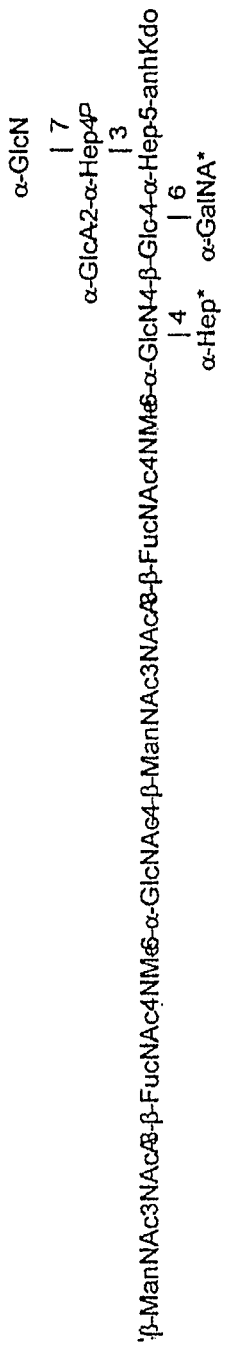
Figure 3:
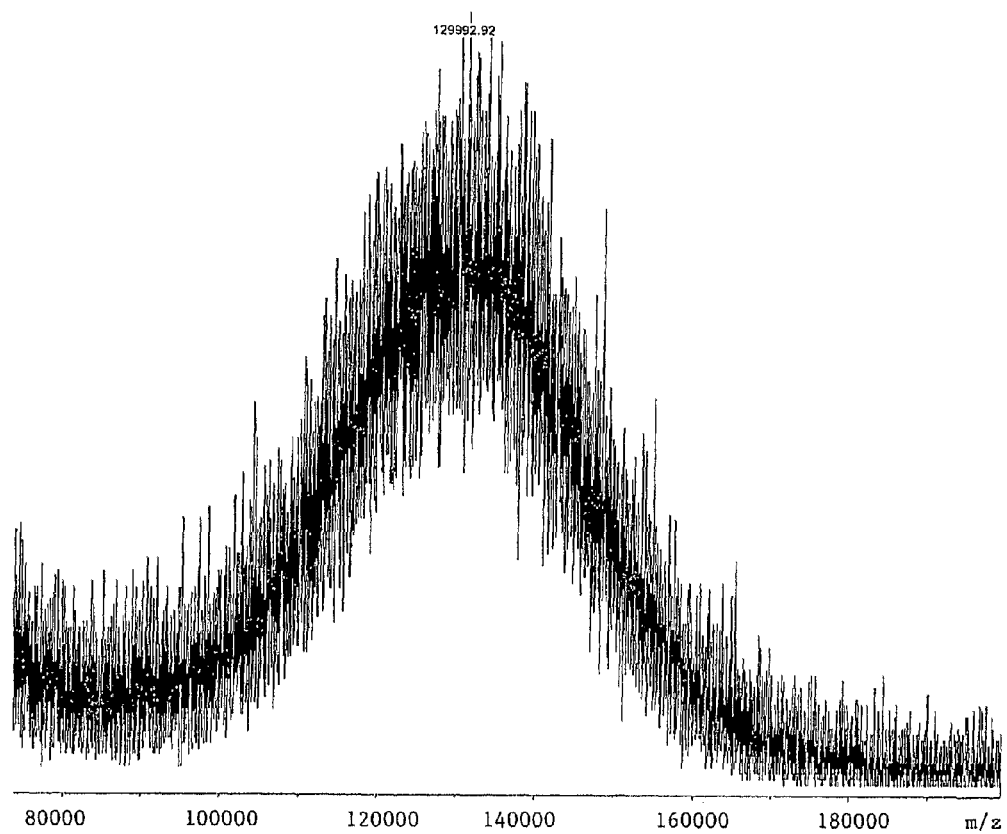
FIG. 3 is a MALDI-TOF spectrum of BSA-ONH$_2$/BbRb50 (conjugate #2 in Table 2 below).
Figure 4:
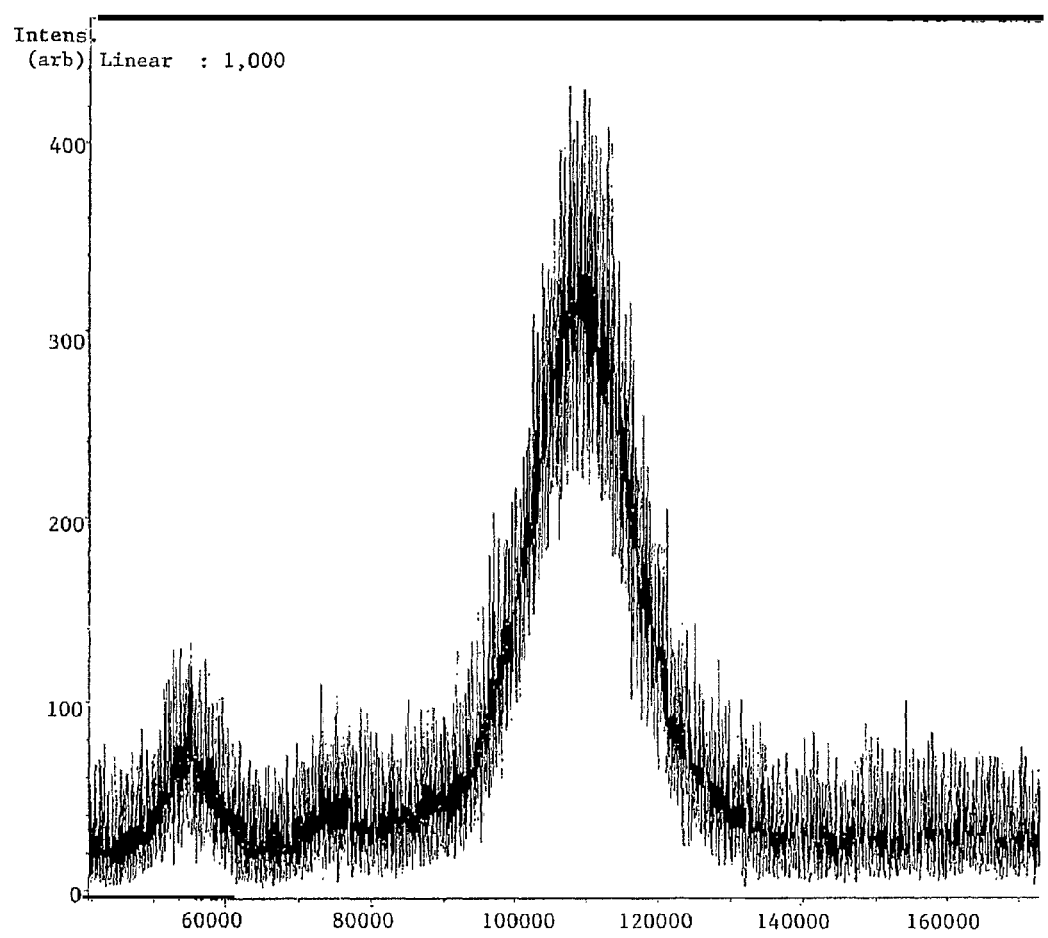
FIG. 4 is a MALDI-TOF spectrum of BSA-ONH$_2$/OS (*H. ducreyi*) (conjugate #1 in Table 4 below).
Figure 5:
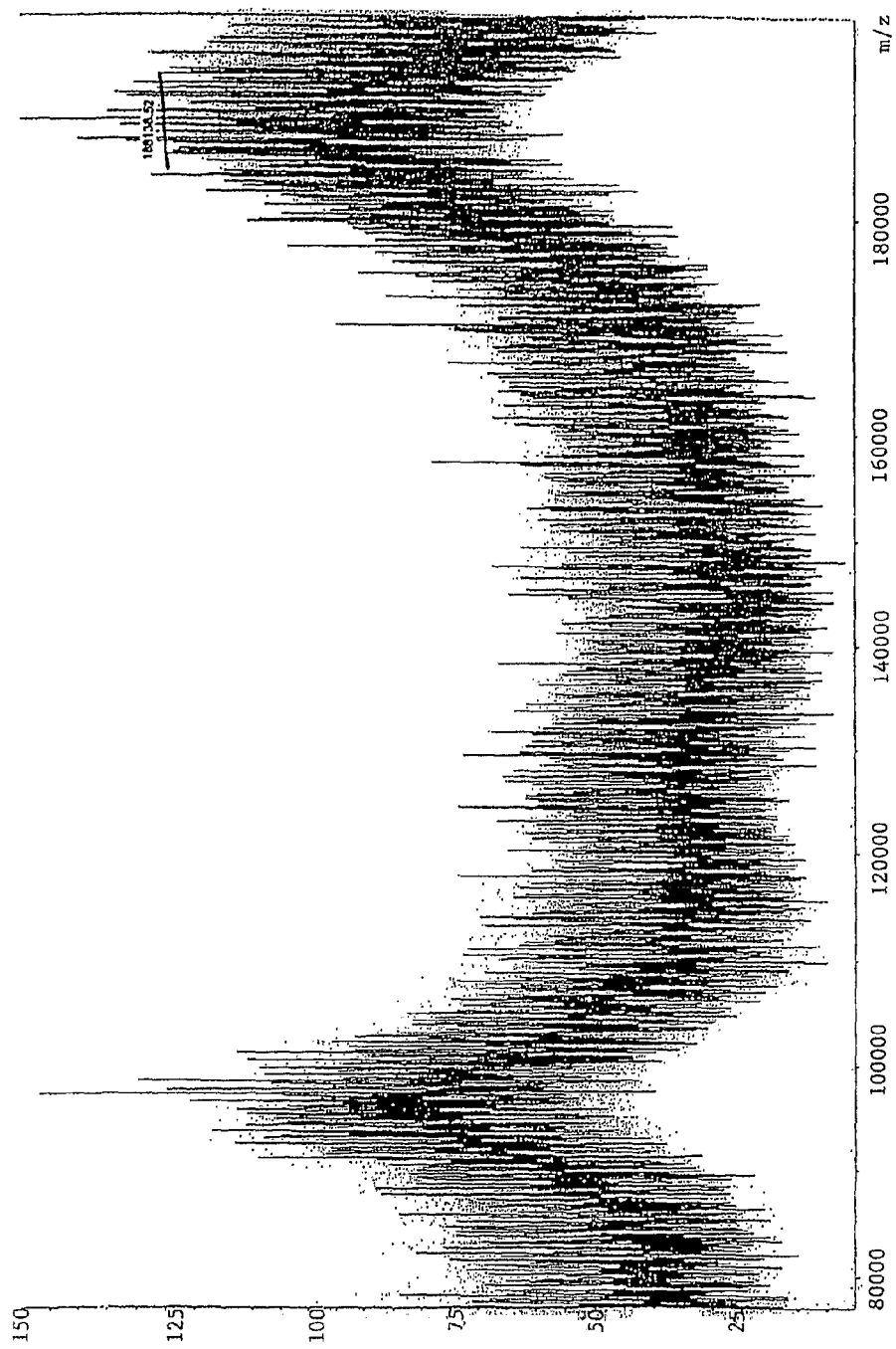
FIG. 5 is a MALDI-TOF spectrum of TT-ONH$_2$/OS (*H. ducreyi*) (conjugate #2 in Table 4 below).
Figure 6:
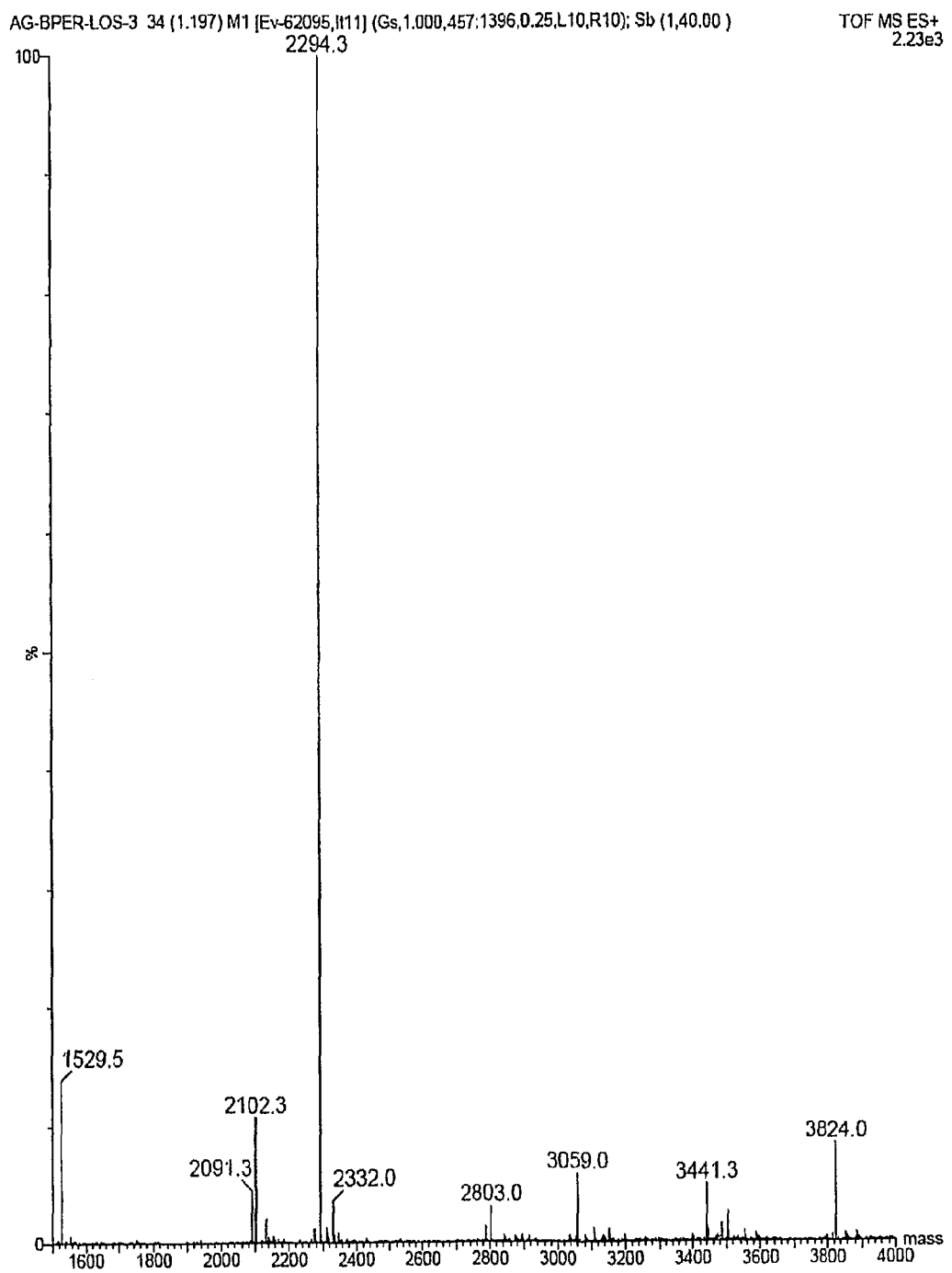
FIG. 6 is an ESI-MS spectrum of *B. pertussis* OS used for conjugation in Example 3.
Figure 7:
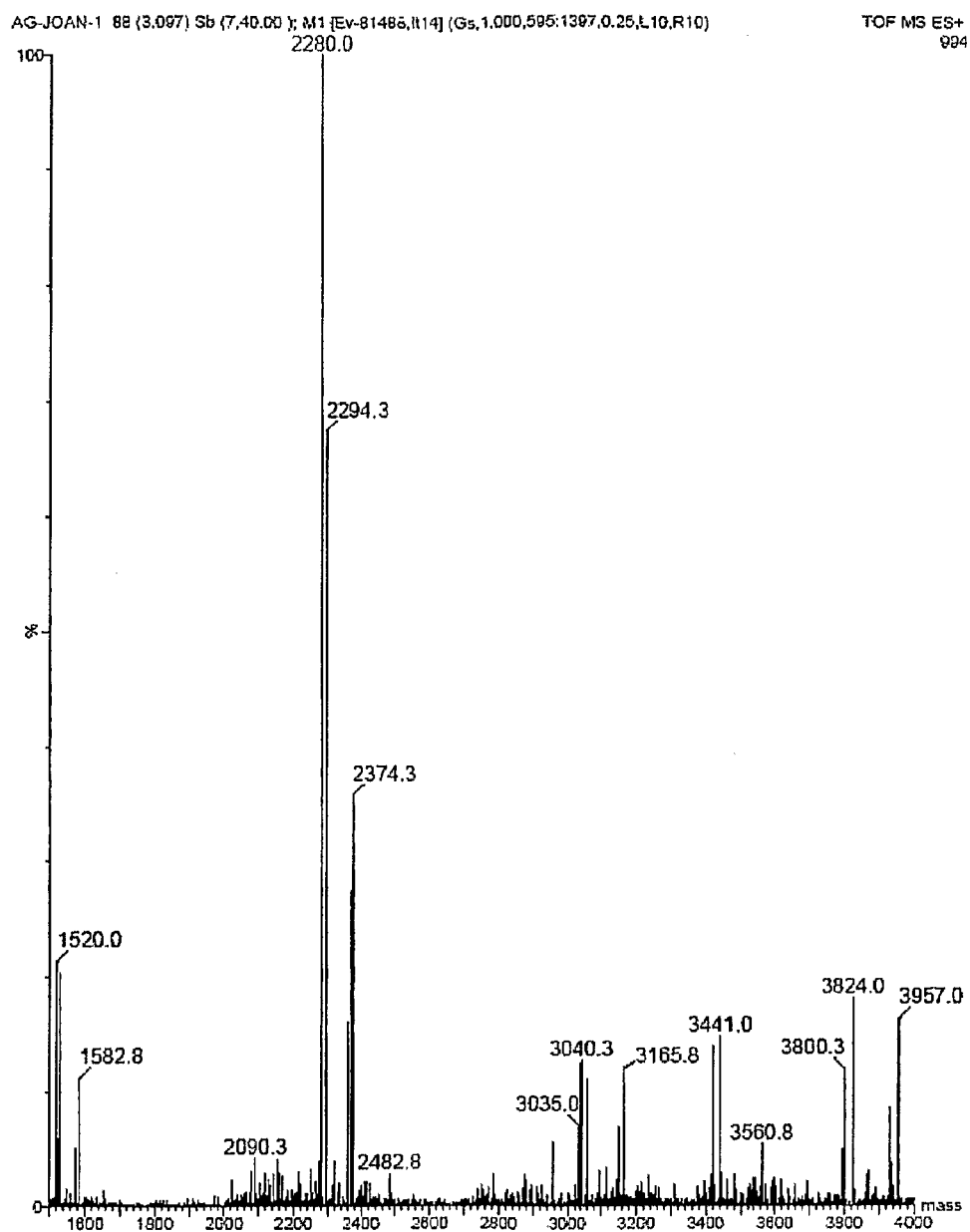
FIG. 7 is an ESI-MS spectrum for *B. bronchiseptica* OS-core used for conjugation in Example 3.

B. bronchiseptica LPS contains the same core structure as B. pertussis but it could be further substituted by O-specific chains. For this study only free core, with no O-SP was used, after separation on BioGel P-4 column. First fraction eluted from the column contained core substituted with O-SP and second fraction contains free core used in this study. ESI-MS (FIGS. 6 and 7) and NMR analysis confirmed the above structure with small variations in case of B. bronchiseptica: the methylation of Fuc4NMe is only 50% (2280 kDa pick), while in B. pertussis is 100% and Hep is phosphorylated in about 30% (2374 Da pick), while in B. pertussis Hep is not phosphorylated.

Conjugates.

SDS-PAGE gel and Maldi analysis showed increase in molecular mass of both conjugates to average 94 kDa comparing to BSA-ONH$_2$ 71 kDa. Since the mass of OS is 2295 Da, the increase indicates average incorporation of 10 OS chains per one BSA molecule in both cases.

Both conjugates reacted with anti-B. pertussis hyperimmune serum and anti-BSA serum with an observed line of identity. Both conjugates induced serum antibody responses on a similar level as assayed by ELISA against B. pertussis LOS.

Example 4

S. flexnarii 2a Conjugates

Methods:

Bacteria and Cultivation.

Shigella flexneri type 2a strain 2457T was grown in ultrafiltered Triptic Soy Broth (Difco Laboratories) with 5 g of glucose and 5 mM magnesium sulphate per liter, for 20 h at 20° C. with stirring and aeration; the pH was maintained at ~7.5 by addition of ammonium hydroxide. The identity of bacteria was confirmed by culture, Gram staining and agglutination with typing antisera. LPS was extracted by hot phenol method and after dialysis recovered from each phase.

Oligosaccharides.

The LPSs (20-80 mg) were treated with 1% acetic acid at 100° C. for 1 h, precipitate of lipid A removed by centrifugation, O-specific chain (O-SP) was separated by gel chromatography on Sephadex G-50 column.

Conjugation.

BSA-ONH$_2$/OS. Bovine serum albumin (BSA, Sigma, St. Louis, Mo.) was derivatized to aminooxylated derivatives in a two step procedure as described in Kielb et al., J. Org. Chem. 70:6987-6990, 2005, which is incorporated herein by reference in its entirety. (1) BSA was treated with succinimidyl 3-(bromoacetamido)propionate (SBAP, Pierce, Pittsburgh, Pa.) to introduce thiol-reactive bromoacetamido moieties (BSA-Br); (2) BSA-Br was coupled with O-(3-thiopropyl) hydroxylamine, a heterobifunctional linker, to form the aminooxylated protein through stable thioether linkages (BSA-ONH$_2$). For conjugation with OS, BSA-ONH$_2$ (1 mg) was reacted with 3 mg of O-SP in 0.3 ml Buffer A (PBS, 0.1% glycerol, 5 mM EDTA), at pH 5.7, for 15 hours. Next, it was passed through a 1×100 cm Sephadex G-50 column in 0.2 M NaCl as eluent and the void volume fraction characterized by protein assay, immunodiffusion and SDS-PAGE. The obtained conjugates were named BSA-ONH$_2$/Sf-OSP.
Results:
O-SP:
S. flexneii O-SP contains a core region composed of 10 sugars substituted with a repeating unit:
Core Region:

```
                            PPE           PPE
                             4             4
                             ↓             ↓
RU→Gal-(1→2)-Gal-(1→2)-Glc- (1→3)-β-Glc-(1→3)-L,D-Hep-(1→3)-L,D-Hep-(1→5)-Kdo
                             ↑             ↑
                             3             7
                             |             |
                            β-Glc    GlcNAc-(1→7)-L,D-Hep
```

PPE-phosphoethanolamine; RU-repeating unit
Repeating unit (about 5-15 repeats)

```
      3-OAc            α-D-Glcp-(1 ┐                   6-OAc
        |                          4                     |
→2)-α-L-Rhap-(1 →2)-α-L-Rhap-(1→3)-α-L-Rhap-(1→3)-β-D-GlcpNAc-(1→
```

Conjugates.

SDS-PAGE gel analysis showed increase in molecular mass of a conjugate comparing to BSA-ONH$_2$ to about 250 kDa. The obtained conjugate reacted with anti-*S. flexnerii* 2a hyperimmune serum and anti-BSA serum with an observed line of identity.

In view of the many possible embodiments to which the principles of the disclosed conjugates and methods may be applied, it should be recognized that the illustrated embodiments are only preferred examples and should not be taken as limiting the scope of the invention.

We claim:

1. An immunogenic conjugate comprising the structure of:

Pr-Sp-O—N=C(COOH)-anh-KDO—OS wherein Pr is a carrier protein, Sp is an optional spacer moiety, anh-KDO is an anhydro moiety from 3-deoxy-D-manno-octulosonic acid, and OS is an oligosaccharide or polysaccharide residue from the cleavage of Lipid A from a lipopolysaccharide, wherein the lipopolysaccharide is obtained from *Haemophilus ducreyi, Bordetella bronchiseptica, Bordetetla parapertussis, Bordetella pertussis, Vibrio cholerae, Haemophilus influenza,* or a mixture thereof.

2. The conjugate of claim 1, wherein the oligosaccharide or polysaccharide includes an O-antigen chain and a core oligosaccharide.

3. The conjugate of claim 1, wherein the lipopolysaccharide is obtained from *Bordetella bronchiseptica* or *Bordetella parapertussis* and the OS includes at least:

-4-β-ManNAc3ANcAN-4-β-GlcNAc3NAcAN-4-β-GalNAc-4-β-ManNAc3NAcA-3-β-FucNAc4NMe-.

4. A pharmaceutical composition comprising the conjugate of claim 3 and a pharmaceutically acceptable carrier.

5. The conjugate of claim 1, wherein the lipopolysaccharide is obtained from *Haemophilus ducreyi* and the OS includes at least:

Hex$_3$HexNAcHep$_4$.

6. The conjugate of claim 1, wherein the oligosaccharide or polysaccharide is obtained from *Bordetella bronchiseptica, Bordetella parapertussis,* or *Bordetella pertussis*.

7. The conjugate of claim 1, wherein the oligosaccharide or polysaccharide is obtained from *Bordetella bronchiseptica* or *Bordetella pertussis*.

8. The conjugate of claim 1, wherein the oligosaccharide or polysaccharide is obtained from *Bordetella parapertussis*.

9. A pharmaceutical composition comprising the conjugate of claim 1 and a pharmaceutically acceptable carrier.

10. The conjugate of claim 1, wherein the lipopolysaccharide is obtained from *Bordetella bronchiseptica*.

11. A pharmaceutical composition comprising the conjugate of claim 10 and a pharmaceutically acceptable carrier.

12. The conjugate of claim 1, wherein there are 5 to 20 OS chains bound to the single carrier protein.

13. The conjugate of claim 1, wherein the OS is not oxidized.

14. A method of eliciting an immune response in a subject, comprising administering to the subject the conjugate of claim 1, thereby eliciting an immune response in the subject.

15. An immunogenic conjugate comprising:
    an oligosaccharide or polysaccharide having a core oligosaccharide, wherein the oligosaccharide or polysaccharide is obtained from *Bordetella bronchiseptica, Bordetella parapertussis, Bordetella pertussis,* or a mixture thereof; and
    a carrier protein,
    wherein the oligosaccharide or polysaccharide is conjugated to the carrier protein via an oxime covalent bond with a 3-deoxy-D-manno-octulsonic acid moiety located at the terminal reducing end of the oligosaccharide or polysaccharide.

16. The conjugate of claim 15, wherein the oligosaccharide or polysaccharide is not oxidized.

* * * * *